US008551973B2

(12) United States Patent  
Bao et al.

(10) Patent No.: US 8,551,973 B2
(45) Date of Patent: Oct. 8, 2013

(54) NUCLEOSIDE ANALOGS

(75) Inventors: Donghui Bao, Grapevine, TX (US); Wonsuk Chang, Princeton, NJ (US); Dhanapalan Nagarathnam, Bethany, CT (US); Michael Joseph Sofia, Doylestown, PA (US)

(73) Assignee: Gilead Pharmasset LLC, Foster City, CA (US)

( * ) Notice: Subject to any disclaimer, the term of this patent is extended or adjusted under 35 U.S.C. 154(b) by 56 days.

(21) Appl. No.: 12/645,710

(22) Filed: Dec. 23, 2009

(65) Prior Publication Data

US 2010/0286083 A1 Nov. 11, 2010

Related U.S. Application Data

(60) Provisional application No. 61/140,441, filed on Dec. 23, 2008.

(51) Int. Cl.
*A01N 43/04* (2006.01)
*A61K 31/70* (2006.01)
*C07H 19/04* (2006.01)
*C07H 19/20* (2006.01)

(52) U.S. Cl.
USPC .......... 514/48; 514/51; 536/26.1; 536/26.7; 536/26.8

(58) Field of Classification Search
None
See application file for complete search history.

(56) References Cited

U.S. PATENT DOCUMENTS

| | | |
|---|---|---|
| 2,512,572 A | 6/1950 | Smith, Jr. |
| 2,563,707 A | 8/1951 | Cosulich |
| 3,053,865 A | 9/1962 | Taub et al. |
| 3,097,137 A | 7/1963 | Beer et al. |
| 3,104,246 A | 9/1963 | Amiard et al. |
| 3,480,613 A | 11/1969 | Walton |
| 3,524,844 A | 8/1970 | Keller-Juslen et al. |
| 3,590,028 A | 6/1971 | Arcamone et al. |
| 3,798,209 A | 3/1974 | Witkowski et al. |
| 3,888,843 A | 6/1975 | Mizuno et al. |
| 3,923,785 A | 12/1975 | Ryder et al. |
| 3,929,992 A | 12/1975 | Sehgal et al. |
| 3,991,045 A | 11/1976 | Ishida et al. |
| 3,994,974 A | 11/1976 | Murakami et al. |
| 4,046,878 A | 9/1977 | Patelli et al. |
| 4,058,519 A | 11/1977 | Arcamone et al. |
| 4,107,423 A | 8/1978 | Arcamone et al. |
| RE29,835 E | 11/1978 | Witkowski et al. |
| 4,197,249 A | 4/1980 | Murdock et al. |
| 4,199,574 A | 4/1980 | Schaeffer |
| 4,203,898 A | 5/1980 | Cullinan et al. |
| 4,210,745 A | 7/1980 | Montgomery |
| 4,303,785 A | 12/1981 | Umezawa et al. |
| 4,307,100 A | 12/1981 | Langlois et al. |
| 4,323,573 A | 4/1982 | Schaeffer |
| 4,355,032 A | 10/1982 | Verheyden et al. |
| 4,418,068 A | 11/1983 | Jones |
| 4,572,912 A | 2/1986 | Yoshioka et al. |
| 4,604,463 A | 8/1986 | Miyasaka et al. |
| 4,673,668 A | 6/1987 | Ishizumi et al. |
| 4,724,232 A | 2/1988 | Rideout et al. |
| 4,753,935 A | 6/1988 | Nelson et al. |
| 4,760,137 A | 7/1988 | Robins et al. |
| 4,797,285 A | 1/1989 | Barenholz et al. |
| 4,808,614 A | 2/1989 | Hertel |
| 4,808,716 A | 2/1989 | Hol et al. |
| 4,814,470 A | 3/1989 | Colin et al. |
| 4,814,477 A | 3/1989 | Wijnberg et al. |
| 4,861,870 A | 8/1989 | Oppico et al. |
| 4,880,784 A | 11/1989 | Robins et al. |
| 4,918,179 A | 4/1990 | Watanabe et al. |
| 4,923,986 A | 5/1990 | Murakata et al. |
| 4,957,924 A | 9/1990 | Beauchamp |
| 5,004,758 A | 4/1991 | Boehm et al. |
| 5,013,556 A | 5/1991 | Woodle et al. |
| 5,026,687 A | 6/1991 | Yarchoan et al. |
| 5,034,394 A | 7/1991 | Daluge |
| 5,041,246 A | 8/1991 | Garrison |
| 5,075,445 A | 12/1991 | Jarvest et al. |
| 5,077,056 A | 12/1991 | Bally et al. |
| 5,077,057 A | 12/1991 | Szoka, Jr. |
| 5,091,188 A | 2/1992 | Haynes |
| 5,104,888 A | 4/1992 | Yoshioka et al. |
| 5,118,820 A | 6/1992 | Hertel |
| 5,130,421 A | 7/1992 | Starrett, Jr. et al. |
| 5,137,918 A | 8/1992 | Weiershausen et al. |
| 5,145,684 A | 9/1992 | Liversidge et al. |
| 5,149,794 A | 9/1992 | Yatvin et al. |
| 5,154,930 A | 10/1992 | Popescu et al. |
| 5,157,027 A | 10/1992 | Biller et al. |

(Continued)

FOREIGN PATENT DOCUMENTS

BE 799805 A1 11/1973
BE 842930 A1 10/1976

(Continued)

OTHER PUBLICATIONS

Byrn et al. Solid-State Chemistry of Drugs, 2d, Chapter 11 Hydrates and Solvates, 233-247, 1999.*
Morissette et al. Adv. Drug Delivery Rev. 2004, 56, 275-300.*
A.M. Rouhi, Chem. & Eng. News, Feb. 24, 2003, 81(8), 32-35.*
Hecker et al., Prodrugs of Phosphates and Phosphonates, J. Med. Chem., 2008, 51: 2328-2345.*
Hecker et al., Prodrugs of Phosphates and Phosphonates, J. Med. Chem. (2008) 51: 2328-2345.
Chou et al., Evidence that Human Histidine Triad Nucleotide Binding Protein 3 (Hint3) is a Distinct Branch of the Histidine Triad (HIT) Superfamily, J. Mol. Biol. (2007) 373: 978-989.
Chou et al., Phosphoramidate Pronucleotides: A Comparison of the Phosphoramidase Substrate Specificity of Human and *Escherichia coli* Histidine Triad Nucleotide Binding Proteins, Mol. Pharm. (2007) 4: 208-217.
Chou et al., 31P NMR and Genetic Analysis Establish hinT as the Only *Escherchia coli* Purine Nucleoside Phosphoramidase and as Essential for Growth under High Salt Conditions, J. Biol. Chem. (2005) 280: 15356-15361.

(Continued)

*Primary Examiner* — Traviss C McIntosh, III
(74) *Attorney, Agent, or Firm* — Fitzpatrick, Cella, Harper & Scinto

(57) ABSTRACT

A purified compound having activity against hepatitis C virus is disclosed.

10 Claims, No Drawings

(56) References Cited

U.S. PATENT DOCUMENTS

| | | |
|---|---|---|
| 5,192,549 A | 3/1993 | Barenolz et al. |
| 5,194,654 A | 3/1993 | Hostetler et al. |
| 5,196,438 A | 3/1993 | Martin et al. |
| 5,206,244 A | 4/1993 | Zahler et al. |
| 5,213,804 A | 5/1993 | Martin et al. |
| 5,223,263 A | 6/1993 | Hostetler et al. |
| 5,225,212 A | 7/1993 | Martin et al. |
| 5,246,937 A | 9/1993 | Harnden et al. |
| 5,256,641 A | 10/1993 | Yatvin et al. |
| 5,277,914 A | 1/1994 | Szoka, Jr. |
| 5,316,771 A | 5/1994 | Barenholz et al. |
| 5,372,808 A | 12/1994 | Blatt et al. |
| 5,376,380 A | 12/1994 | Kikuchi et al. |
| 5,405,598 A | 4/1995 | Schinazi et al. |
| 5,411,947 A | 5/1995 | Hostetler et al. |
| 5,420,266 A | 5/1995 | Britton et al. |
| 5,462,724 A | 10/1995 | Schinazi et al. |
| 5,463,092 A | 10/1995 | Hostetler et al. |
| 5,484,926 A | 1/1996 | Dressman et al. |
| 5,494,911 A | 2/1996 | Bartlett et al. |
| 5,496,546 A | 3/1996 | Wang et al. |
| 5,538,865 A | 7/1996 | Reyes et al. |
| 5,538,975 A | 7/1996 | Dionne |
| 5,543,389 A | 8/1996 | Yatvin et al. |
| 5,543,390 A | 8/1996 | Yatvin et al. |
| 5,543,391 A | 8/1996 | Yatvin et al. |
| 5,549,910 A | 8/1996 | Szoka, Jr. |
| 5,554,728 A | 9/1996 | Basava et al. |
| 5,567,434 A | 10/1996 | Szoka, Jr. |
| 5,610,054 A | 3/1997 | Draper |
| 5,620,985 A | 4/1997 | Jacquesy et al. |
| 5,633,358 A | 5/1997 | Gruetzke et al. |
| 5,633,388 A | 5/1997 | Diana et al. |
| 5,635,517 A | 6/1997 | Muller et al. |
| 5,676,942 A | 10/1997 | Testa et al. |
| 5,695,784 A | 12/1997 | Pollinger et al. |
| 5,703,058 A | 12/1997 | Schinazi et al. |
| 5,711,944 A | 1/1998 | Gilbert et al. |
| 5,719,147 A | 2/1998 | Dorn et al. |
| 5,725,859 A | 3/1998 | Omer |
| 5,736,155 A | 4/1998 | Bally et al. |
| 5,738,845 A | 4/1998 | Imakawa |
| 5,738,846 A | 4/1998 | Greenwald et al. |
| 5,747,646 A | 5/1998 | Hakimi et al. |
| 5,767,097 A | 6/1998 | Tam |
| 5,792,834 A | 8/1998 | Hakimi et al. |
| 5,827,533 A | 10/1998 | Needham |
| 5,830,455 A | 11/1998 | Valtuena et al. |
| 5,830,905 A | 11/1998 | Diana et al. |
| 5,834,594 A | 11/1998 | Hakimi et al. |
| 5,837,257 A | 11/1998 | Tsai et al. |
| 5,846,964 A | 12/1998 | Ozeki |
| 5,849,696 A | 12/1998 | Chretien et al. |
| 5,852,195 A | 12/1998 | Romines et al. |
| 5,869,253 A | 2/1999 | Draper |
| 5,882,679 A | 3/1999 | Needham |
| 5,891,468 A | 4/1999 | Martin et al. |
| 5,891,874 A | 4/1999 | Colacino et al. |
| 5,905,070 A | 5/1999 | Schinazi et al. |
| 5,908,621 A | 6/1999 | Glue et al. |
| 5,922,757 A | 7/1999 | Chojkier |
| 5,925,643 A | 7/1999 | Chu |
| 5,928,636 A | 7/1999 | Alber et al. |
| 5,942,223 A | 8/1999 | Bazer et al. |
| 5,980,884 A | 11/1999 | Blatt et al. |
| 5,990,276 A | 11/1999 | Zhang et al. |
| 6,004,933 A | 12/1999 | Spruce et al. |
| 6,034,134 A | 3/2000 | Gold et al. |
| 6,043,077 A | 3/2000 | Barber et al. |
| 6,056,961 A | 5/2000 | Lavie et al. |
| 6,060,080 A | 5/2000 | Kikuchi et al. |
| 6,090,932 A | 7/2000 | McGee et al. |
| 6,130,326 A | 10/2000 | Ramasamy et al. |
| 6,132,763 A | 10/2000 | Fisher |
| 6,143,321 A | 11/2000 | Needham et al. |
| 6,156,501 A | 12/2000 | McGall et al. |
| 6,174,905 B1 | 1/2001 | Suzuki et al. |
| 6,180,134 B1 | 1/2001 | Zalipsky et al. |
| 6,200,598 B1 | 3/2001 | Needham |
| 6,214,375 B1 | 4/2001 | Modi |
| 6,224,903 B1 | 5/2001 | Martin et al. |
| 6,232,300 B1 | 5/2001 | Schinazi et al. |
| 6,239,159 B1 | 5/2001 | Brown et al. |
| 6,267,985 B1 | 7/2001 | Chen et al. |
| 6,294,192 B1 | 9/2001 | Patel et al. |
| 6,296,870 B1 | 10/2001 | Needham et al. |
| 6,320,078 B1 | 11/2001 | Suzuki et al. |
| 6,348,587 B1 | 2/2002 | Schinazi |
| 6,372,883 B1 | 4/2002 | Attwood et al. |
| 6,383,471 B1 | 5/2002 | Chen et al. |
| 6,391,859 B1 | 5/2002 | Schinazi et al. |
| 6,395,300 B1 | 5/2002 | Straub et al. |
| 6,410,531 B1 | 6/2002 | Llinas-Brunet et al. |
| 6,420,380 B2 | 7/2002 | Llinas-Brunet et al. |
| 6,455,513 B1 | 9/2002 | McGuigan |
| 6,455,690 B1 | 9/2002 | Tam et al. |
| 6,479,463 B1 | 11/2002 | Wang et al. |
| 6,495,677 B1 | 12/2002 | Ramasamy et al. |
| 6,509,320 B1 | 1/2003 | Wang et al. |
| 6,534,523 B1 | 3/2003 | Llinas-Brunet et al. |
| 6,552,183 B1 | 4/2003 | Ramasamy et al. |
| 6,552,197 B2 | 4/2003 | Kamihara et al. |
| 6,555,677 B2 | 4/2003 | Petrillo et al. |
| 6,569,463 B2 | 5/2003 | Patel et al. |
| 6,573,248 B2 | 6/2003 | Ramasamy et al. |
| 6,620,325 B2 | 9/2003 | Fuenfschilling et al. |
| 6,635,278 B1 | 10/2003 | Dahl et al. |
| 6,642,206 B2 | 11/2003 | Ramasamy et al. |
| 6,645,528 B1 | 11/2003 | Straub et al. |
| 6,653,455 B1 | 11/2003 | Johdo et al. |
| 6,660,721 B2 | 12/2003 | Devos et al. |
| 6,677,314 B2 | 1/2004 | Klecker et al. |
| 6,677,315 B2 | 1/2004 | Klecker et al. |
| 6,680,068 B2 | 1/2004 | Campbell et al. |
| 6,680,303 B2 | 1/2004 | Schinazi et al. |
| 6,682,715 B2 | 1/2004 | Klecker et al. |
| 6,683,045 B2 | 1/2004 | Klecker et al. |
| 6,703,374 B1 | 3/2004 | Klecker et al. |
| 6,726,925 B1 | 4/2004 | Needham |
| 6,753,309 B2 | 6/2004 | Klecker et al. |
| 6,777,395 B2 | 8/2004 | Bhat |
| 6,787,305 B1 | 9/2004 | Li et al. |
| 6,787,526 B1 | 9/2004 | Bryant et al. |
| 6,812,219 B2 | 11/2004 | LaColla |
| 6,815,542 B2 | 11/2004 | Hong et al. |
| 6,897,201 B2 | 5/2005 | Boyer et al. |
| 6,908,924 B2 | 6/2005 | Watanabe et al. |
| 6,911,424 B2 | 6/2005 | Schinazi |
| 6,914,054 B2 | 7/2005 | Sommadossi |
| 6,923,988 B2 | 8/2005 | Patel et al. |
| 6,932,983 B1 | 8/2005 | Straub et al. |
| 6,962,991 B2 | 11/2005 | Dempcy et al. |
| 6,977,257 B2 | 12/2005 | Parab et al. |
| 7,018,985 B1 | 3/2006 | Boyer et al. |
| 7,018,989 B2 | 3/2006 | McGuigan |
| 7,060,294 B2 | 6/2006 | Batra et al. |
| 7,060,689 B2 | 6/2006 | Goins et al. |
| 7,070,801 B2 | 7/2006 | Yamazaki et al. |
| 7,081,449 B2 | 7/2006 | Pietrzkowski et al. |
| 7,105,493 B2 | 9/2006 | Sommadossi |
| 7,105,499 B2 | 9/2006 | Carroll |
| 7,125,855 B2 | 10/2006 | Bhat |
| 7,148,206 B2 | 12/2006 | Sommadossi et al. |
| 7,163,929 B2 | 1/2007 | Sommadossi et al. |
| 7,202,224 B2 | 4/2007 | Eldrup |
| 7,265,152 B2 | 9/2007 | Saha et al. |
| 7,307,065 B2 | 12/2007 | Schinazi |
| 7,323,453 B2 | 1/2008 | Olsen |
| 7,378,402 B2 | 5/2008 | Martin et al. |
| 7,390,791 B2 | 6/2008 | Becker |
| 7,429,572 B2 | 9/2008 | Clark |
| 7,462,608 B2 | 12/2008 | Chen et al. |
| 7,608,597 B2 | 10/2009 | Sommadossi |
| 7,608,600 B2 | 10/2009 | Storer |

| Patent/Pub. No. | Date | Name |
|---|---|---|
| 7,635,689 B2 | 12/2009 | LaColla |
| 7,879,815 B2 | 2/2011 | MacCoss |
| 7,964,560 B2 | 6/2011 | Wang et al. |
| 7,964,580 B2 * | 6/2011 | Sofia et al. .................... 514/51 |
| 8,173,621 B2 | 5/2012 | Du et al. |
| 2002/0058635 A1 | 5/2002 | Averett |
| 2002/0142050 A1 | 10/2002 | Straub et al. |
| 2002/0198173 A1 | 12/2002 | Schinazi et al. |
| 2003/0050229 A1 | 3/2003 | Sommadossi et al. |
| 2003/0060400 A1 | 3/2003 | LaColla et al. |
| 2003/0120071 A1 | 6/2003 | McGuigan et al. |
| 2003/0144502 A1 | 7/2003 | Pietrzkowski et al. |
| 2003/0153744 A1 | 8/2003 | Mekouar et al. |
| 2004/0006007 A1 | 1/2004 | Gosselin et al. |
| 2004/0014108 A1 | 1/2004 | Eldrup et al. |
| 2004/0023240 A1 | 2/2004 | Marliere et al. |
| 2004/0023901 A1 | 2/2004 | Cook et al. |
| 2004/0059104 A1 | 3/2004 | Cook et al. |
| 2004/0063622 A1 | 4/2004 | Sommadossi et al. |
| 2004/0067901 A1 | 4/2004 | Bhat et al. |
| 2004/0072788 A1 | 4/2004 | Bhat et al. |
| 2004/0097461 A1 | 5/2004 | Sommadossi et al. |
| 2004/0097462 A1 | 5/2004 | Sommadossi et al. |
| 2004/0101535 A1 | 5/2004 | Sommadossi et al. |
| 2004/0102414 A1 | 5/2004 | Sommadossi et al. |
| 2004/0110717 A1 | 6/2004 | Carroll et al. |
| 2004/0167140 A1 | 8/2004 | Schinazi et al. |
| 2004/0191824 A1 | 9/2004 | Dempcy et al. |
| 2004/0214844 A1 | 10/2004 | Otto et al. |
| 2004/0224917 A1 | 11/2004 | Dahl et al. |
| 2004/0229839 A1 | 11/2004 | Babu et al. |
| 2004/0248892 A1 | 12/2004 | Wang |
| 2004/0254141 A1 | 12/2004 | Schinazi et al. |
| 2004/0259934 A1 | 12/2004 | Olsen et al. |
| 2004/0265969 A1 | 12/2004 | Li et al. |
| 2004/0266996 A1 | 12/2004 | Rabi |
| 2005/0009737 A1 | 1/2005 | Clark |
| 2005/0026853 A1 | 2/2005 | Mekouar et al. |
| 2005/0031588 A1 | 2/2005 | Sommadossi et al. |
| 2005/0048116 A1 | 3/2005 | Straub et al. |
| 2005/0058710 A1 | 3/2005 | Straub et al. |
| 2005/0075309 A1 | 4/2005 | Storer et al. |
| 2005/0080034 A1 | 4/2005 | Standring et al. |
| 2005/0090660 A1 | 4/2005 | Watanabe et al. |
| 2005/0124532 A1 | 6/2005 | Sommadossi et al. |
| 2005/0130931 A1 | 6/2005 | Boyer et al. |
| 2005/0137161 A1 | 6/2005 | Sommadossi et al. |
| 2005/0142532 A1 | 6/2005 | Poo et al. |
| 2005/0148534 A1 | 7/2005 | Castellino et al. |
| 2005/0164960 A1 | 7/2005 | Olsen et al. |
| 2005/0190931 A1 | 9/2005 | Hsieh |
| 2005/0215513 A1 | 9/2005 | Boojamra et al. |
| 2005/0227947 A1 | 10/2005 | Chen et al. |
| 2005/0261237 A1 | 11/2005 | Boojamra et al. |
| 2006/0003951 A1 | 1/2006 | Mekouar et al. |
| 2006/0014943 A1 | 1/2006 | Dempcy et al. |
| 2006/0034937 A1 | 2/2006 | Patel |
| 2006/0035866 A1 | 2/2006 | Cannizzaro et al. |
| 2006/0040944 A1 | 2/2006 | Gosselin et al. |
| 2006/0057196 A1 | 3/2006 | Hussain et al. |
| 2006/0079478 A1 | 4/2006 | Boojamra et al. |
| 2006/0110727 A9 | 5/2006 | McGall et al. |
| 2006/0122146 A1 | 6/2006 | Chun et al. |
| 2006/0122154 A1 | 6/2006 | Olsen et al. |
| 2006/0142238 A1 | 6/2006 | McGuigan |
| 2006/0144502 A1 | 7/2006 | Weder |
| 2006/0165655 A1 | 7/2006 | Babu et al. |
| 2006/0188570 A1 | 8/2006 | Batra et al. |
| 2006/0276511 A1 | 12/2006 | Serrano-Wu et al. |
| 2007/0015905 A1 | 1/2007 | LaColla et al. |
| 2007/0026073 A1 | 2/2007 | Doney |
| 2007/0037735 A1 | 2/2007 | Gosselin et al. |
| 2007/0037773 A1 | 2/2007 | Sommadossi et al. |
| 2007/0042939 A1 | 2/2007 | LaColla et al. |
| 2007/0042988 A1 | 2/2007 | Klumpp et al. |
| 2007/0042990 A1 | 2/2007 | Gosselin et al. |
| 2007/0059360 A1 | 3/2007 | Jaiswal et al. |
| 2007/0060498 A1 | 3/2007 | Gosselin et al. |
| 2007/0060541 A1 | 3/2007 | Gosselin et al. |
| 2007/0077295 A1 | 4/2007 | Dahl et al. |
| 2007/0087960 A1 | 4/2007 | Storer et al. |
| 2007/0099902 A1 | 5/2007 | Dahl et al. |
| 2007/0197463 A1 | 8/2007 | Chun |
| 2007/0225249 A1 | 9/2007 | Shi |
| 2007/0265222 A1 | 11/2007 | MacCoss et al. |
| 2007/0275912 A1 | 11/2007 | Bhat |
| 2008/0014228 A1 | 1/2008 | Darmuzey et al. |
| 2008/0070861 A1 | 3/2008 | Clark |
| 2008/0139802 A1 | 6/2008 | Axt et al. |
| 2008/0253995 A1 | 10/2008 | Clark |
| 2008/0261913 A1 | 10/2008 | Sommadossi et al. |
| 2008/0286230 A1 | 11/2008 | Sommadossi et al. |
| 2008/0300200 A1 | 12/2008 | Babu et al. |
| 2009/0004135 A1 | 1/2009 | Clark |
| 2009/0036666 A1 | 2/2009 | Clark |
| 2009/0169504 A1 | 7/2009 | Sommadossi et al. |
| 2009/0306007 A1 | 12/2009 | Wagner |
| 2009/0317361 A1 | 12/2009 | Cho et al. |
| 2010/0016251 A1 | 1/2010 | Sofia et al. |
| 2010/0016252 A1 | 1/2010 | Keana et al. |
| 2010/0021425 A1 | 1/2010 | Butler et al. |
| 2010/0022468 A1 | 1/2010 | Meppen |
| 2010/0035835 A1 | 2/2010 | Narjes |
| 2010/0056770 A1 | 3/2010 | Axt et al. |
| 2010/0081628 A1 | 4/2010 | Du et al. |
| 2010/0152128 A1 | 6/2010 | Attenni |
| 2010/0173863 A1 | 7/2010 | Schinazi |
| 2010/0234316 A1 | 9/2010 | Maccoss et al. |
| 2010/0234584 A1 | 9/2010 | Chang |
| 2010/0256098 A1 | 10/2010 | Appella et al. |
| 2010/0279973 A1 | 11/2010 | Chun et al. |
| 2010/0286083 A1 | 11/2010 | Bao et al. |
| 2010/0298257 A1 | 11/2010 | Ross et al. |
| 2010/0316594 A1 | 12/2010 | Sommadossi |
| 2011/0015146 A1 | 1/2011 | Sofia et al. |
| 2011/0038833 A1 | 2/2011 | Clark |
| 2011/0070194 A1 | 3/2011 | Cho et al. |
| 2011/0124592 A1 | 5/2011 | McGuigan |
| 2011/0245484 A1 | 10/2011 | Ross et al. |
| 2011/0251152 A1 | 10/2011 | Ross et al. |
| 2011/0257121 A1 | 10/2011 | Chang et al. |
| 2011/0257122 A1 | 10/2011 | Sofia et al. |
| 2011/0286962 A1 | 11/2011 | Sommadossi et al. |
| 2011/0293563 A1 | 12/2011 | Butler et al. |
| 2012/0254824 A1 | 10/2012 | Bansod |

FOREIGN PATENT DOCUMENTS

| | | |
|---|---|---|
| BE | 898506 A1 | 4/1984 |
| CA | 956939 A1 | 10/1974 |
| CA | 995608 | 8/1976 |
| CN | 101108870 A | 1/2008 |
| DE | 2426304 A1 | 1/1975 |
| DE | 2510866 A1 | 10/1975 |
| DE | 2517596 A1 | 10/1975 |
| DE | 2539963 A1 | 3/1976 |
| DE | 2835661 A1 | 3/1979 |
| DE | 19914474 A1 | 10/1999 |
| EP | 0014853 A1 | 9/1980 |
| EP | 0062503 A1 | 10/1982 |
| EP | 0107486 A1 | 5/1984 |
| EP | 0173059 A2 | 3/1986 |
| EP | 0180276 A1 | 5/1986 |
| EP | 0184162 A2 | 6/1986 |
| EP | 0206459 A2 | 12/1986 |
| EP | 0206497 A2 | 12/1986 |
| EP | 0219829 A2 | 4/1987 |
| EP | 0242851 A1 | 10/1987 |
| EP | 0253738 A1 | 1/1988 |
| EP | 0321122 A2 | 6/1989 |
| EP | 0349242 A2 | 1/1990 |
| EP | 0350287 A2 | 1/1990 |
| EP | 0432695 A2 | 6/1991 |
| EP | 0495432 A1 | 7/1992 |
| EP | 0503537 A1 | 9/1992 |
| EP | 0737686 A1 | 4/1995 |
| FR | 2707988 A1 | 1/1995 |
| GB | 768821 A | 2/1957 |
| GB | 985598 A | 3/1965 |

| | | | | | | | |
|---|---|---|---|---|---|---|---|
| GB | 1209654 | A | 10/1970 | WO | 03/062256 | A1 | 7/2003 |
| GB | 1449708 | | 9/1976 | WO | 03/066885 | A2 | 8/2003 |
| GB | 2004293 | A | 3/1979 | WO | 03/068244 | A1 | 8/2003 |
| GB | 2133005 | A | 7/1984 | WO | 03/101993 | A1 | 12/2003 |
| GB | 2136425 | A | 9/1984 | WO | 03/105770 | A2 | 12/2003 |
| JP | 47016483 | U | 10/1972 | WO | 03/106477 | A1 | 12/2003 |
| JP | 58219196 | A | 12/1983 | WO | 2004/000858 | A2 | 12/2003 |
| JP | 60-19790 | A | 1/1985 | WO | 2004/002422 | A2 | 1/2004 |
| SU | 508076 | A1 | 10/1976 | WO | 2004/002999 | A2 | 1/2004 |
| WO | 88/07045 | A1 | 9/1988 | WO | 2004/003000 | A2 | 1/2004 |
| WO | 89/02733 | A1 | 4/1989 | WO | 2004/003138 | A1 | 1/2004 |
| WO | 90/00555 | A1 | 1/1990 | WO | 2004/007512 | A2 | 1/2004 |
| WO | 91/16920 | A1 | 11/1991 | WO | 2004/009020 | A2 | 1/2004 |
| WO | 91/17159 | A1 | 11/1991 | WO | 2004/009610 | A2 | 1/2004 |
| WO | 91/17748 | A1 | 11/1991 | WO | 2004/011478 | A2 | 2/2004 |
| WO | 91/18914 | A1 | 12/1991 | WO | 2004/014313 | A2 | 2/2004 |
| WO | 91/19721 | A1 | 12/1991 | WO | 2004/014852 | A2 | 2/2004 |
| WO | 92/10497 | A1 | 6/1992 | WO | 2004/035571 | A1 | 4/2004 |
| WO | 92/14743 | A2 | 9/1992 | WO | 2004/046331 | A2 | 6/2004 |
| WO | 93/00910 | A1 | 1/1993 | WO | 2004/058792 | A1 | 7/2004 |
| WO | 94/09010 | A1 | 4/1994 | WO | 2004/080466 | A1 | 9/2004 |
| WO | 94/26273 | A1 | 11/1994 | WO | 2004/096234 | A2 | 11/2004 |
| WO | 95/09843 | A1 | 4/1995 | WO | 2004/096235 | A2 | 11/2004 |
| WO | 95/13090 | A1 | 5/1995 | WO | 2004/096286 | A2 | 11/2004 |
| WO | 95/16679 | A1 | 6/1995 | WO | 2004/106356 | A1 | 12/2004 |
| WO | 95/24185 | A1 | 9/1995 | WO | 2005/000864 | A1 | 1/2005 |
| WO | 95/30670 | A2 | 11/1995 | WO | 2005/002626 | A2 | 1/2005 |
| WO | 96/15132 | A1 | 5/1996 | WO | 2005/003147 | A2 | 1/2005 |
| WO | 96/32403 | A2 | 10/1996 | WO | 2005/007810 | A2 | 1/2005 |
| WO | 97/36554 | A1 | 10/1997 | WO | 2005/008877 | A1 | 1/2005 |
| WO | 97/42949 | A1 | 11/1997 | WO | 2005/009418 | A2 | 2/2005 |
| WO | 98/09964 | A1 | 3/1998 | WO | 2005/012327 | A2 | 2/2005 |
| WO | 98/13344 | A1 | 4/1998 | WO | 2005/020884 | A2 | 3/2005 |
| WO | 98/16184 | A2 | 4/1998 | WO | 2005/021568 | A2 | 3/2005 |
| WO | 98/17679 | A1 | 4/1998 | WO | 2005/067900 | A2 | 7/2005 |
| WO | 98/22496 | A2 | 5/1998 | WO | 2005/072361 | A2 | 8/2005 |
| WO | 98/54185 | A1 | 12/1998 | WO | 2005/087788 | A2 | 9/2005 |
| WO | 99/07734 | A2 | 2/1999 | WO | 2006/000922 | A2 | 1/2006 |
| WO | 99/15194 | A1 | 4/1999 | WO | 2006/012078 | A2 | 2/2006 |
| WO | 99/32139 | A1 | 7/1999 | WO | 2006/012440 | A2 | 2/2006 |
| WO | 99/32140 | A1 | 7/1999 | WO | 2006/029081 | A2 | 3/2006 |
| WO | 99/43691 | A1 | 9/1999 | WO | 2006/031725 | A2 | 3/2006 |
| WO | 99/59621 | A1 | 11/1999 | WO | 2006/035061 | A1 | 4/2006 |
| WO | 99/64016 | A1 | 12/1999 | WO | 2006/037028 | A2 | 4/2006 |
| WO | 00/06529 | A1 | 2/2000 | WO | 2006/050161 | A2 | 5/2006 |
| WO | 00/09531 | A2 | 2/2000 | WO | 2006/061576 | A1 | 6/2006 |
| WO | 00/24355 | A1 | 5/2000 | WO | 2006/065335 | A2 | 6/2006 |
| WO | 00/32153 | A1 | 6/2000 | WO | 2006/100310 | A1 | 9/2006 |
| WO | 01/32153 | A2 | 5/2001 | WO | 2006/100439 | A1 | 9/2006 |
| WO | 01/60315 | A2 | 8/2001 | WO | 2006/120251 | A1 | 11/2006 |
| WO | 01/79246 | A2 | 10/2001 | WO | 2006/120252 | A2 | 11/2006 |
| WO | 01/81359 | A1 | 11/2001 | WO | 2006/121820 | A1 | 11/2006 |
| WO | 01/90121 | A2 | 11/2001 | WO | WO2006121820 | | 11/2006 |
| WO | 01/91737 | A2 | 12/2001 | WO | 2007/002191 | A2 | 1/2007 |
| WO | 01/92282 | A2 | 12/2001 | WO | 2007/027248 | A2 | 3/2007 |
| WO | 01/96353 | A2 | 12/2001 | WO | 2007/038507 | A2 | 4/2007 |
| WO | 02/08187 | A1 | 1/2002 | WO | 2007/069923 | A1 | 6/2007 |
| WO | 02/08198 | A2 | 1/2002 | WO | 2007/070556 | A2 | 6/2007 |
| WO | 02/08251 | A2 | 1/2002 | WO | 2007/095269 | A2 | 8/2007 |
| WO | 02/08256 | A2 | 1/2002 | WO | 2008/024843 | A2 | 2/2008 |
| WO | 02/18404 | A2 | 3/2002 | WO | 2008/045419 | A1 | 4/2008 |
| WO | 02/32414 | A2 | 4/2002 | WO | 2008/082601 | A2 | 7/2008 |
| WO | 02/32920 | A2 | 4/2002 | WO | 2008/121634 | A2 | 10/2008 |
| WO | 02/42172 | A1 | 5/2002 | WO | 2009/009951 | A1 | 1/2009 |
| WO | 02/48116 | A2 | 6/2002 | WO | 2009/029844 | A1 | 3/2009 |
| WO | 02/48157 | A2 | 6/2002 | WO | 2009/067409 | A1 | 5/2009 |
| WO | 02/48165 | A2 | 6/2002 | WO | 00/37110 | A2 | 6/2009 |
| WO | 02/48172 | A2 | 6/2002 | WO | 2009/132123 | A1 | 10/2009 |
| WO | 02/491165 | A1 | 6/2002 | WO | 2009/152095 | A2 | 12/2009 |
| WO | 02/057287 | A2 | 7/2002 | WO | 2010/075517 | A2 | 7/2010 |
| WO | 02/057425 | A2 | 7/2002 | WO | 2010/075549 | A2 | 7/2010 |
| WO | 02/060926 | A2 | 8/2002 | WO | 2010/075554 | A1 | 7/2010 |
| WO | 02/100415 | A2 | 12/2002 | WO | 2010/081082 | A2 | 7/2010 |
| WO | 02/104415 | A2 | 12/2002 | WO | 2010/135569 | A1 | 11/2010 |
| WO | 03/011877 | A2 | 2/2003 | WO | 2011/035231 | A1 | 3/2011 |
| WO | 03/024461 | A1 | 3/2003 | ZA | 66/7585 | | 12/1965 |
| WO | 03/051899 | A1 | 6/2003 | ZA | 68/2378 | | 4/1967 |
| WO | 03/053989 | A1 | 7/2003 | | | | |
| WO | 03/061576 | A2 | 7/2003 | | | | |

OTHER PUBLICATIONS

Aquaro et al., Antimicrobial Agents and Chemotherapy (2000) 1: 173-177.
Chapman et al., Nucleotides, Nucleosides and Nucleic Acids (2001) 20(4-7): 621-628.
Chapman et al., Nucleotides, Nucleosides and Nucleic Acids (2001) 20(4-7): 1085-1090.
Clark et al., J. Med. Chem. (2005) 48(17): 5504-5508.
Eisenberg et al., Nucleosides, Nucleotides & Nucleic Acids (2001) 20(4-7): 1091-1098.
Howes et al. Nucleosides, Nucleotides and Nucleic Acids (2003) 22(5): 687-689.
Lee et al., Antimicrobial Agents and Chemotherapy (2005) 49(5): 1898-1906.
Ma et al., J. Biol. Chem. (2007) 282(41): 29812-29820.
McGuigan et al., Antiviral Chemistry and Chemotherapy (1998) 9: 473-479.
Murakami et al., Antiviral Chemistry & Chemotherapy (2007) 51(2): 503-509.
Murakami et al., Antimicrobial Agents and Chemotherapy (2008) 52(2): 458-464.
Perrone et al., J. Med. Chem. (2007) 50(8): 1840-1849.
Ray et al., Antimicrobial Agents and Chemotherapy (2008) 52(2): 648-654.
Stuyver et al., Antiviral Chemistry & Chemotherapy (2004) 48(2): 651-654.
International Search Report and Written Opinion of the International Searching Authority issued in PCT/US2009/069420, mailed May 8, 2012 (16 pages).
International Preliminary Report on Patentability issued in PCT/US2009/069420, mailed May 18, 2012 (2 pages).
Cahard, D., et al., "Aryloxy Phosphoramidate Triesters as Pro-Tides," Mini-reviews in Medicinal Chemistry, vol. 4, No. 4, pp. 371-381 (2004).
Murakami, E., et al., "The Mechanism of Action of B-D-2'-Deoxy-2'-Fluoro-2'-C-Methylcytidine Involves a Second Metabolic Pathway Leading to B-D-2'-Deoxy-2'-Fluoro-2'-C-Methyluridine 5'-Triphosphate, a Potent Inhibitor of the Hepatitis C Virus RNA-Dependant RNA Polymerase," Antimicrobial Agents and Chemotherapy, vol. 52, No. 2, pp. 458-464 (2008).
Stella, V.J., "Prodrugs as Therapeutics," Expert Opinion Ther. Patents, vol. 14, No. 3, pp. 277-280 (2004).
D.M. Lehsten, et al., "An Improved Procedure for the Synthesis of Nucleoside Phosphoramidates", Org. Proc. Res. & Dev. 2002, 6, 819-822.
Asif, G. et al., "Pharmacokinetics of the Antiviral Agent B-D-2'-Deoxy-2'-Fluoro-2'-C-Methycytidine in Rhesus Monkeys," Antimicrobial Agents and Chemotherapy, vol. 51, No. 8, pp. 2877-2882 (2007).
Jantzen et al., "Prodrugs," Modern Pharmaceutics, Banker, G.S. et al. 3rd ed., Marcel Dekker, Inc., pp. 596.
Battaglia, A.M. et al., "Combination Therapy with Interferon and Ribavirin in the Treatment of Chronic Hepatitis C Infection," the Annals of Pharmacotherapy, vol. 34, pp. 487-494 (2000).
Berenguer, M. et al., "Hepatitis C Virus in the Transplant Setting," Antiviral Therapy 3 (Supplement 3), pp. 126-136 (1997).
Chawla, G. et al., "Challenges in Polymorphism of Pharmaceuticals," CRIPS, vol. 5, No. 1, pp. 9-12 (2004).
Bhat, B. et al., "Synthesis and Pharmacokinetic Properties of Nucleoside Analogues as Possible Inhibitors of HCV RNA Replication," Antiviral Research, Abstract No. 120, vol. 57, No. 3, p. A75 (2003).
Chu, M. et al., "Structure of Sch 68631: A New Hepatitis C Virus Proteinase Inhibitor from Streptomyces sp.," Tetrahedron Letters, vol. 37, No. 40, pp. 7229-7232 (1996).
De Lombaert, S. et al., "N-Phosphonomethyl Dipeptides and Their Phosphonate Prodrugs, a New Generation of Neutral Endopeptidase (NEP, EC 3.4.24.11) Inhibitors," Journal of Medicinal Chemistry, vol. 37, No. 4, pp. 498-511 (1994).
Farquhar, D. et al., "Synthesis and Biological Evaluation of 945'-(2-0xo-1,3,2-oxazaphosphorinan-2-yl)-B-D-arabinosyl] adenine and 945'-(2-0xo-1,3,2-dioxaphosphorinan-2-yl)-B-D-arabinosyl]adenine: Potential Neutral Precursors of 9-[Bd-Arabinofuranosyl] 5'-Monophosphate," Journal of Medicinal Chemistry, vol. 28, No. 9, pp. 1358-1361 (1985).
Eldrup, A.B. et al., "Structure Activity Relationship of 2' Modified Nucleosides for Inhibition of Hepatitis C Virus," Antiviral Research, Abstract No. 119, vol. 57, No. 3, p. A75 (2003).
Edmundson, R.S. et al., "Cyclic Organophosphorus Compounds. Part 23. Configurational Assignments in the 4Phenyl-1,3,2-dioxaphosphorinane Series. X-Ray Molecular Structure of cis-2-Benzylamino-4-phenyl-1,3,2- dioxaphosphorinane 2-Oxide," Journal of Chemical Research (S), pp. 122-123 (1989).
Farquhar, D. et al., "Synthesis and Biological Evaluation of Neutral Derivatives of 5-Fluoro-2'-deoxyuridine 5'-Phosphate," Journal of Medicinal Chemistry, vol. 26, No. 8, pp. 1153-1158 (1983).
Chu, M., et al., "Isolation and Structure of Sch 351633: A Novel Hepatitis C Virus (HCV) NS3 Protease Inhibitor from the Fungus Penicillium Griseofulvum," Bioorganic & Medicinal Chemistry Letters, vol. 9, pp. 1949-1952 (1999).
Eldrup, A.B. et al., "Structure-Activity Relationship of Purine Ribonucleosides for Inhibition of Hepatitis C Virus RNA-Dependent RNA Polymerase," Journal of Medicinal Chemistry, vol. 47, No. 9, pp. 2283-2295 (2004).
Davis, G.L., "Current Therapy for Chronic Hepatitis C," Gastroenterology, vol. 118, No. 2, pp. S104-S114 (2000).
Hostetler, K.Y. et al., "Synthesis and Antiretroviral Activity of Phospholipid Analogs of Azidothymidine and Other Antiviral Nucleosides," The Journal of Biological Chemistry, vol. 265, No. 11, pp. 6112-6115 (1990).
Hunston, R.N. et al., "Synthesis and Biological Properties of Some Cyclic Phosphotriesters Derived from 2'-Deoxy-5-Fluorouridine," vol. 27, No. 4, pp. 440-444 (1984).
Haleblian, J.K., "Characterization of Habits and Crystalline Modification of Solids and Their Pharmaceutical Applications," Journal of Pharmaceutical Sciences, vol. 64, No. 8, pp. 1269-1288 (1975).
Kryuchkov, A.A., et al., "Influence of Solvent on the Strength of Cyclic Oxygen-Containing Phosphorus Acids," Bulletin of the Academy of Sciences of the USSR, vol. 36, No. 6, Part 1, pp. 1145-1148 (1987).
Kotra, L.P. et al., "Structure-Activity Relationships of 2'-Deoxy-2'-2'-difluoro-L-erythro-pentofuranosyl Nucleosides," Journal of Medicinal Chemistry, vol. 40, No. 22, pp. 3635-3644 (1997).
Li, N. S. et al., "Synthesis of the Phosphoramidite Derivative of 2'-Deoxy-2'-C-B-methylcytidine," Journal of Organic Chemistry, vol. 68, No. 17, pp. 6799-6802 (2003).
Freed, J.J. et al., "Evidence for Acyloxymethyl Esters of Pyrimidine 5'-Deoxyribonucleotides as Extracellular Sources of Active 5'-Deoxyribonucleotides in Cultured Cells," Biochemical Pharmacology, vol. 38, No. 19, pp. 3193-3198 (1989).
Kucera, L.S. et al., "Novel Membrane-Interactive Ether Lipid Analogs that Inhibit Infectious HIV-1 Production and Induce Defective Virus Formation," AIDS Research and Human Retroviruses, vol. 6, No. 4, pp. 491-501 (1990).
Hostetler, K.Y. et al., "Greatly Enhanced Inhibition of Human Immunodeficiency Virus Type 1 Replication in CEM and HT4-6C Cells by 3'-Deoxythymidine Diphosphate Dimyristoylglycerol, a Lipid Prodrug of 3'-Deoxythymidine," Antimicrobial Agents and Chemotherapy, vol. 36, No. 9, pp. 2025-2029 (1992).
Khamnei, S. et al., "Neighboring Group Catalysis in the Design of Nucleotide Prodrugs, Journal of Medicinal Chemistry," vol. 39, No. 20, pp. 4109-4115 (1996).
Jones, R.J. et al., "Minireview: Nucleotide Prodrugs," Antiviral Research, vol. 27, pp. 1-17 (1995).
Hertel, L.W. et al., "Synthesis of 2-Deoxy-2,2-difluoro-D-ribose and 2-Deoxy-2,2-difluoro-D-ribofuranosyl Nucleosides," Journal of Organic Chemistry, vol. 53, No. 11, pp. 2406-2409 (1988).
Neidlein, R. et al., "Mild Preparation of 1-Benzyloxyiminoalkylphosphonic Dichlorides: Application to the Synthesis of Cyclic Phosphonic Diesters and Cyclic Monoester Amides," Heterocycles, vol. 35, No. 2, pp. 1185-1203 (1993).
Starrett, Jr., J.E. et al., "Synthesis, Oral Bioavailability Determination, and in Vitro Evaluation of Prodrugs of the Antiviral Agent 9-[2-(Phosphonomethoxy)ethyl]adenine (Pmea)," Journal of Medicinal Chemistry, vol. 37, No. 12, pp. 1857-1864 (1994).

Meier, C. et al., "Cyclic Saligenyl Phosphotriesters of 2',3'-Dideoxy-2',3'-didehydrothymidine (d4T) - A New Pro-Nucleotide Approach," Bioorganic & Medicinal Chemistry Letters, vol. 7, No. 2, pp. 99-104 (1997).

Piantadosi, C. et al., "Synthesis and Evaluation of Novel Ether Lipid Nucleoside Conjugates for Anti-Hiv-1 Activity," Journal of Medicinal Chemistry, vol. 34, No. 4, pp. 1408-1414 (1991).

Shih, Y.E. et al., "Preparation and Structures of 2-Dimethylamino-4-phenyl-1,3,2-dioxaphosphorinane-2-oxides," Bull. Inst. Chem. Academia Sinica, No. 41, pp. 9-16 (1994).

Mitchell, A.G. et al., "Bioreversible Protection for the Phospho Group: Bioactivation of the Di(4-acyloxybenzyl) and Mono(4-acyloxybenzyl) Phosphoesters of Methylphosphonate and Phosphonoacetate," Journal of the Chemical Society, Perkin Transactions, pp. 2345-2353 (1992).

Otto, M.J., "Evaluation of nucleoside analogs in the hepatitis C virus replicon system," Framing the Knowledge of Therapeutics for Viral Hepatitis, Schmazi and Schiff, eds., pp. 247-261 (2006).

Nifantyev, E.E. et al., "Synthesis and Structure of Some Stable Phospholane-Phospholanes," Phosphorus, Sulfur, and Silicon, vol. 113, pp. 1-13 (1996).

Olsen, D.B. et al., "2.-Modified Nucleoside Analogs as Inhibitors of Hepatitis C RNA Replication," Program and Abstracts of Sixteenth Intl Conf. on Antiviral Research, Abstract No. 121, vol. 57, No. 3, p. A76 (2003).

Stuyver, L.J. et al., "Ribonucleoside Analogue That Blocks Replication of Bovine Viral Diarrhea and Hepatitis C Viruses in Culture," Antimicrobial Agents and Chemotherapy, vol. 47, No. 1, pp. 244-254 (2003).

Barnett, C.J. et al., "Structure-Activity Relationships of Dimeric Catharanthus Alkaloids. 1. Deacetylvinblastine Amide (Vindesine) Sulfate,"Journal of Medicinal Chemistry, vol. 21, No. 1, pp. 88-96 (1978).

Andrews, R.C. et al., "Asymmetric Total Synthesis of (-)-Podophyllotoxin," J. Am. Chem. Soc., vol. 110, No. 23, pp. 7854-7858 (1988).

Arcamone, F. et al., "Adriamycin, 14-Hydroxydaunomycin, a New Antitumor Antobiotic from S. peucetius var. caesius," Biotechnology and Bioengineering, vol. XI, pp. 1101-1110 (1969).

Arcamone, F. et al., "Synthesis and Antitumor Properties of New Glycosides of Daunomycinone and Adriamycinone," Journal of Medicinal Chemistry, vol. 18, No. 7, pp. 703-707 (1975).

Arcamone, F. et al., "Synthesis and antitumor activity of new daunorubicin and adriamycin analogues," Experientia, vol. 34, No. 10, pp. 1255-1257 (1978).

Arnold, A.M. et al., "Etoposide: A New Anti-Cancer Agent," the Lancet, vol. 2, pp. 912-915 (1981).

Ashton, W.T. et al., "Activation by Thymidine Kinase and Potent Antiherpetic Activity of 2'-Nor-2'-Deoxyguanosine (2'NDG)," Biochemical and Biophysical Research Communications, vol. 108, No. 4, pp. 1716-1721 (1982).

Bauta, W.E. et al., "A New Process for Antineoplastic Agent Clofarabine," Organic Process Research & Development, vol. 8, No. 6, pp. 889-896 (2004).

Baker, D.C. et al., "Studies Related to the Total Synthesis of Pentostatin. Approaches to the Synthesis of (8R)-3,6,7,8Tetrahydroimidazo-[4,5-d][1,3]diazepin-8-ol and N-3 Alkyl Congeners (la)," J. Heterocyclic Chem., vol. 20, pp. 629-633 (1983).

Balzarini, J. et al., "Mechanism of anti-Hiv action of masked alaninyl d4T-MP derivatives," Proc. Natl. Acad. Sci., vol. 93, pp. 7295-7299 (Jul. 1996).

Brands, K M J: et al."Efficient Synthesis of NK1 Receptor Antagonist Aprepitant Using a Crystallization-Induced Diasteroselective Transformation," J. Am. Chem. Soc., vol. 125, pp. 2129-2135 (2003).

Bush, E.J. et al., "Asymmetric Total Synthesis of (-)-Podophyllotoxin," J. Chem. Soc., Chem. Commun., pp. 1200-1201 (1993).

Brox, L.W. et al., "Studies on the Growth Inhibition and Metabolism of 2'-Deoxy-2'-fluorocytidine in Cultured Human Lymphoblasts," Cancer Research, vol. 34, pp. 1838-1842 (1974).

Yoshioka, T. et al., "Studies on Hindered Phenols and Analogues. 1. Hypolipidemic and Hypoglycemic Agents with Ability to Inhibit Lipid Peroxidation," J. Med. Chem., vol. 32, No. 2, pp. 421-428 (1989).

Zee-Cheng, R.K.Y. et al., "Antineoplastic Agents. Structure-Activity Relationship Study of Bis(substituted aminoalkylamino)anthraquinones," J. Med. Chem., vol. 21, No. 3, pp. 291-294 (1978).

Sorbera, L.A. et al., "SDZ-RAD," Drugs of the Future, vol. 24, No. 1, pp. 22-29 (1999).

Oxford, A.E. et al., "CXCIX. Studies in the Biochemistry of Micro-Organisms," BioChenn. J., vol. 27, pp. 1473-1478 (1933).

Clutterbuck, P.W. et al., "LXXXVI. Studies in the Biochemistry of Micro-Organisms," Biochem. J., vol. 27, pp. 654-667 (1933).

Clutterbuck, P.W. et al., "CLXXI. Studies in the Biochemistry of Micro-Organisms," Biochem. J., vol. 26, pp. 1441-1458 (1932).

McGuigan, C. et al., "Phosphoramidate ProTides of 2'-C-Methylguanosine as Highly Potent Inhibitors of Hepatitis C Virus. Study of Their in Vitro and in Vivo Properties," J. Med. Chem., vol. 53, No. 13, pp. 4949-4957 (2010).

Mizuno, K. et al., "Studies on Bredinin. I Isolation, Characterization and Biological Properties," The Journal of Antibiotics, vol. 27, No. 10, pp. 775-782 (1974).

Fahy, J. et al., "Vinca Alkaloids in Superacidic Media: a Method for Creating a New Family of Antitumor Derivatives," J. Am. Chem. Soc., vol. 119, No. 36, pp. 8576-8577 (1997).

Matsumoto, H. et al., "A Convenient Synthesis of 9-(2-Hydroxyethoxymethyl)guanine (Acyclovir) and Related Compounds," Chem. Pharm. Bull., vol. 36, No. 3, pp. 1153-1157 (1988).

Gauze, G.F. et al., "Production of Antitumor Antibiotic Carminomycin by Actinomadura Carminata Sp. Nov.," pp. 675-678 (1973).

Moncrief, J.W. et al., "Structures of Leurocristine (Vincristine) and Vincaleukoblastine. X-Ray Analysis of Leurocristine Methiodide," J. Am. Chem. Soc., vol. 87, No. 21, pp. 4963-4964 (1965).

Cahard, D. et al., "Aryloxy Phosphoramidate Triesters as Pro-Tides," Mini-Reviews in Medicinal Chemistry, vol. 4, No. 4, pp. 371-381 (2004).

Knaggs, M.H. et al., "A QSAR Study Investigating the Effect of L-Alanine Ester Variation on the Anti-HIV Activity of Some Phosphoramidate Derivatives of d4T," Bioorganic & Medicinal Chemistry Letters, vol. 10, No. 18, pp. 2075-2078 (2000).

Zon, G., Ph.D., "Cyclophosphamide Analogues," Progress in Medicinal Chemistry, vol. 19, pp. 205-246 (1982).

Wolff, M.E., "Some Considerations for Prodrug Design," Burger's Medicinal Chemistry and Drug Discovery, vol. 1, pp. 975-977 (5th ed. 1995).

Stuyver, L.J. et al., "Dynamics of Subgenomic Hepatitis C Virus Replicon Rna Levels in Huh-7 Cells after Exposure to Nucleoside Antimetabolites," Journal of Virology, vol. 77, No. 19, pp. 10689-10694 (2003).

Byrn, S.R. et al., "Hydrates and Solvates," Solid-State Chemistry of Drugs, Chapter 11, pp. 233-247 (2nd ed. 1999).

Rouhi, A.M. et al., "The Right Stuff," Chemical & Engineering News, vol. 81, No. 8, pp. 32-35 (2003).

Byrn, S. et al., "Pharmaceutical Solids: A Strategic Approach to Regulatory Considerations," Pharmaceutical Research, vol. 12, No. 7, pp. 945-954 (1995).

Morissette, S.L. et al., "High-throughput crystallization: polymorphs, salts, co-crystals and solvates of pharmaceutical solids," Advanced Drug Delivery Reviews, vol. 56, pp. 275-300 (2004).

McGuigan, C. et al., "Anti-cancer ProTides: tuning the activity of Bvdu phosphoramidates related to thymectacin," Bioorganic & Medicinal Chemistry, vol. 13, pp. 3219-3227 (2005).

Ben-Hattar, J. et al., "Facile Synthesis of Base-Labile 2'-Deoxyribonucleosides: An Improved Synthesis of 2'-Deoxy-5-Aza-Cytidine," Nucleosides & Nucleotides, vol. 6, Nos. 1 & 2, pp. 393-394 (1987).

Brazhnikova, M.G. et al., "Physical and Chemical Characteristics and Structure of Carminomycin, A New Antitumor Antibiotic," the Journal of Antibiotics, vol. XXVII, No. 4, pp. 254-259 (1974).

Berman, J.D. et al., "Activity of Purine Analogs Against Leishmania Donovani in Vivo," Antimicrobial Agents and Chemotherapy, vol. 31, No. 1, pp. 111-113 (1987).

Beach, J. W. et al., "Synthesis of Enantiomerically Pure (2'R, 5'S)-(-)[2-(Hydroxymethyl)oxathiolan-5-yl]cytosine as a Potent Antiviral Agent against Hepatitis B Virus (HBV) and Human Immunodeficiency Virus (HIV)," J. Org. Chem, vol. 57, pp. 2217-2219 (1992).

Crimmins, M.T. et al., "An Efficient Asymmetric Approach to Carbocyclic Nucleosides: Asymmetric Synthesis of 1592U89, a Potent Inhibitor of Hiv Reverse Transcriptase," J. Org. Chem., vol. 61, No. 13, pp. 4192-4193 (1996).

Chou, T.S. et al., "Stereospecific Synthesis of 2-Deoxy-2,2-difluororibonolactone and Its Use in the Preparation of 2'Deoxy-2',2'-difluoro-B-D-ribofuranosyl Pyrimidine Nucleosides: The Key Role of Selective Crystallization," Synthesis, pp. 565-570 (Jun. 1992).

Cosulich, D.B. et al., "Analogs of Pteroylglutamic Acid. I.," J. Am. Chem. Soc., vol. 70, pp. 1922-1926 (1948).

Clark, J.L. et al., "Design, Synthesis, and Antiviral Activity of 2'-Deoxy-2'-fluoro-2'-C-methylcytidine, a Potent Inhibitor of Hepatitis C Virus Replication," J. Med. Chem., vol. 48, No. 17, pp. 5504-5508 (2005).

Chan, E. et al., "Total Synthesis of (8R)-3-(2-Deoxy-B-D-erythropentofuranosyl)-3,6,7,8-tetrahydroimidazo[4,5-d][1,3] diazepin-8-ol (Pentostatin), the Potent Inhibitor of Adenosine Deaminase," J. Org. Chem., vol. 47, No. 18, pp. 3457-3464 (1982).

Chu, C.K. et al., "An Efficient Total Synthesis of 3'-Azido-3'-Deoxythymidine (Azt) and 3'-Azido-2', 3'-Dideoxyuridine (AZDDU, CS-87) From D-Mannitol," Tetrahedron Letters, vol. 29, No. 42, pp. 5349-5352 (1988).

Christensen, L.F. et al., "Synthesis and Biological Activity of Selected 2,6-Disubstituted-(2-Deoxy-a-and -6-D-erythropentofuranosyl)purines," J. Med. Chem., vol. 15, No. 7, pp. 735-739 (1972).

Di Marco, A. et al., "Daunomycin, a New Antibiotic of the Rhodomycin Group," Nature, vol. 201, pp. 706-707 (Feb. 15, 1964).

Erion, M.D., "Prodrugs for Liver-targeted Drug Delivery," Biotechnology: Pharmaceutical Aspects, vol. V, pp. 541-572 (2007).

Eldrup, A.B. et al., "Structure-Activity Relationship of Heterobase-Modified 2'-C-Methyl Ribonucleosides as Inhibitors of Hepatitis C Virus Rna Replication," J. Med. Chem., vol. 47, No. 21, pp. 5284-5297 (2004).

Evans, C.A. et al., "Divergent Asymmetric Syntheses of Dioxolane Nuccleoside Analogues," Tetrahedron: Asymmetry, vol. 4, No. 11, pp. 2319-2322 (1993).

Fors, K.S. et al., "A Convergent, Scalable Synthesis of HIV Protease Inhibitor PNU-140690," J. Org. Chem., vol. 63, No. 21, pp. 7348-7356 (1998).

Fretz, H. et al., "Rapamycin and FK506 Binding Proteins (Immunophilins)," J. Am. Chem. Soc., vol. 113, pp. 1409-1411 (1991).

Fukukawa, K. et al., "Synthesis of Bredinin From 5-Aminoimidazole-4-Carboamide-Ribofuranoside (Aica-riboside)," Chem. Phaim. Bull., vol. 32, No. 4, pp. 1644-1646 (1984).

Guillory, J.K., "Generation of Polymorphs, Hydrates, Solvates, and Amorphous Solids," Polymorphism in Pharmaceutical Solids, pp. 183-226 (1999).

Goris, N. et al., "2'-C-Methylcytidine as potent and selective inhibitor of the replication of foot-and-mouth disease virus," Antiviral Research, vol. 73, pp. 161-168 (2007).

Gorman, M. et al., "Vinca Alkaloids. IV. Structural Features of Leurosine and Vincaleukoblastine, Representatives of a New Type of Indole-Indoline Alkaloids," J. Am. Chem. Soc., vol. 81, pp. 4745-4746 (1959).

Glinski, R.P. et al., "Nucleotide Synthesis. IV. Phosphorylated 3'-Amino-3'-deoxythymidine and 5'-Amino-5'- deoxythymidine and Derivatives," J. Org. Chem., vol. 38, No. 25, pp. 4299-4305 (1973).

Gorman, M. et al., "Vinca Alkaloids III. Characterization of Leurosine and Vincaleukoblastine, New Alkaloids From Vinca Rosea Linn," J. Am. Chem. Soc., vol. 81, pp. 4754-4755 (1959).

Gensler, W.J. et al., "Synthesis of Podophyllotoxin," J. Am. Chem. Soc., vol. 84, pp. 1748-1749 (1962).

Holy, A. et al., "Synthesis of 9-(2-Phosphonylmethoxyethyl)Adenine and Related Compounds," Collection Czechoslovak Chem. Comm., vol. 52, pp. 2801-2809 (1987).

Hale, J.J. et al., "Structural Optimization Affording 2-(R)-(1-(R)-3,5-Bis(trifluoromethyl)phenylethoxy)-3-(S)-(4-fluoro) phenyl-4-(3-oxo-1,2,4-triazol-5-yl)methylmorpholine, a Potent, Orally Active, Long-Acting Morpholine Acetal Human NK-1 Receptor Antagonist," J. Med. Chem., vol. 41, No. 23, pp. 4607-4614 (1998).

Hannah, J. et al., "Carba-acyclonucleoside Antiherpetic Agents," J. Heterocyclic Chem., vol. 26, pp. 1261-1271 (1989).

Holton, R.A. et al., "First Total Synthesis of Taxol. 2. Completion of the C and D Rings," J. Am. Chem. Soc., vol. 116, pp. 1599-1600 (1994).

Horwitz, J.P. et al., "Nucleosides. V. The Monomesylates of 1-(2'-Deoxy-B-D-lyxofuranosyl)thymine," J. Org. Chem., vol. 29, pp. 2076-2078 (1964).

Holton, R.A. et al., "First Total Synthesis of Taxol. 1. Functionalization of the B Ring," J. Am. Chem. Soc., vol. 116, pp. 1597-1598 (1994).

Harnden, M.R. et al., "Synthesis and Antiviral Activity of 9-[4-Hydroxy-3-(hydroxymethyl)but-1-yl]purines," J. Med. Chem., vol. 30, No. 9, pp. 1636-1642 (1987).

Horwitz, J.P. et al.' "Nucleosides. IX. The Formation of 2',3'-Unsaturated Pyrimidine Nucleosides via a Novel B-Elimination Reaction," J. Org. Chem., vol. 31, pp. 205-211 (1966).

Horwitz, J.P. et al., "Nucleosides. XI. 2',3'-Dideoxycytidine," J. Org. Chem., vol. 32, pp. 817-818 (1967).

Hayashi, M. et al., "Studies on Bredinin. III. Chemical Synthesis of Bredinin (a Novel Imidazole Nucleoside)," Chem. Pharm. Bull., vol. 23, No. 1, pp. 245-246 (1975).

Humber, D.C. et al., "Expeditious Preparation of (-)-2'-Deoxy-3'-Thiacytidine (3TC)," Tetrahedron Letters, vol. 33, No. 32, pp. 4625-4628 (1992).

Holy, A. et al., "Synthesis of Enantiomeric N-(2-Phosphonomethoxypropyl) Derivatives of Purine and Pyrimidine Bases. II. The Synthon Approach," Collect. Czech. Chem. Commun., vol. 60, pp. 1390-1409 (1995).

Hostetler, K.Y. et al., "Synthesis and Antiretroviral Activity of Phospholipid Analogs of Azidothymidine and Other Antiviral Nucleosides," the Journal of Biological Chemistry, vol. 265, No. 11, pp. 6112-6117 (1990).

Jones, T.K. et al., "Total Synthesis of the Immunosuppressant (-)-Fk-506," J. Am. Chem. Soc., vol. 111, No. 3, pp. 1157-1159 (1989).

Jones, C.D. et al., "Antiestrogens. 2. Structure-Activity Studies in a Series of 3-Aroyl-2-arylbenzo[b]thiophene Derivatives Leading to [6-Hydroxy-2-(4-hydroxypheny)benzo[b]thien-3-yl][4-[2-(1-piperidinyl)ethoxy]-phenyl]methanone Hydrochloride (LY156758), a Remarkably Effective Estrogen Antagonist with Only Minimal Intrinsic Estrogencity," J. Med. Chem., vol. 27, No. 8, pp. 1057-1066 (1984).

Jenkins, S.R. et al., "Branched-Chain Sugar Nucleosides. IV. 2'-C-Methyladenosine," J. Org. Chem., vol. 33, No. 6, pp. 2490-2494 (1968).

Jeong, L.S. et al., "Asymmetric Synthesis and Biological Evaluation of B-L-(2R,5R)-and α-L-(2R,5R)-1,3-OxathiolanePyrimidine and -Purine Nucleosides as Potential Anti-Hiv Agents," J. Med. Chem., vol. 36, No. 2, pp. 181-195 (1993).

Ikehara, M. et al., "Studies of Nucleosides and Nucleotides. XXIV. Purine Cyclonucleosides. I. 8,2'-Cyclonucleoside Derived from 2-Chloro-8-mercapto-9-B-D-xylofuranosyladenine," J. Am. Chem. Soc., vol. 87, No. 3, pp. 606-610 (1965).

Ikehara, M. et al., "A New Type of 'Cyclonucleoside' Derived from 2-Chloro-8-mercapto-9-B-D-xylofuranosyladenine," J. Am. Chem. Soc., vol. 85, pp. 2344-2345 (1963).

Kahl, R., "The Liver," Toxicology, Marquardt et al. eds., Chapter 13, pp. 273-296 (1999).

Kryuchkov, A.A. et al., "Influence of Solvent on the Strength of Cyclic Oxygen-Containing Phosphorus Acids," Bull. Of the Academy of Sciences of the Ussr, Division of Chemical Science, vol. 36, No. 6, pp. 1145-1148 (1987).

Kingsbury, W.D. et al., "Synthesis of Water-Soluble (Aminoalkyl)Camptothecin Analogues: Inhibition of Topoisomerase I and Antitumor Activity," J. Med. Chem., vol. 34, No. 1, pp. 98-107 (1991).

Kino, T. et al., "FK-506, a Novel Immunosuppressant Isolated From a Streptomyces," The Journal of Antibiotics, vol. XI, No. 9, pp. 1249-1255 (1987).

Krapcho, A.P. et al., "6,9-Bis[(aminoalkyl)amino]Benzo[g]isoquinoline-5,10-diones. A Novel Class of Chromophore-Modified Antitumor Anthracene-9,10-diones: Synthesis and Antitumor Evaluations," J. Med. Chem., vol. 37, No. 6, pp. 828-837 (1994).

Kazimierczuk, Z. et al., "Synthesis of 2'-Deoxytubercidin, 2'-Deoxyadenosine, and Related 2'-Deoxynucleosides via a Novel Direct Streospecific Sodium Salt Glycosylation Procedure," J. Am. Chem. Soc., vol. 106, No. 21, pp. 6379-6382 (1984).

Kaneko, T. et al., "Total Synthesis of (+) Podophyllotoxin," Tetrahedron Letters, vol. 28, No. 5, pp. 517-520 (1987).

Marumoto, R. et al., "One-Step Halogenation at the 2'-Position of Uridine, and Related Reactions of Cytidine and N4- Acetylcytidine," Chem. Pharm. Bull., vol. 22, No. 1, pp. 128-134 (1974).

Mehellou, Y. et al., "Aryloxy Phosphoramidate Triesters: a Technology for Delivering Monophosphorylated Nucleosides and Sugars into Cells," ChemMedChem, vol. 4, pp. 1779-1791 (2009).

Montgomery, J.A. et al., "An Improved Procedure for the Preparation of 9-B-D-Arabinofuranosyl 1-2-fluoroadenine," J. Heterocyclic Chem., vol. 16, pp. 157-160 (1979).

Montgomery, J.A. et al., "Nucleosides of 2-Fluoroadenine," J. Med. Chem., vol. 12, pp. 498-504 (1969).

Montgomery, J.A. et al., "Synthesis and Biologic Activity of 2'-Flouro-2-halo Derivatives of 9-B-DArabinofuranosyladenine," J. Med. Chem., vol. 35, No. 2, pp. 397-401 (1992).

Mangatal, L. et al., "Application of the Vicinal Oxyamination Reaction with Asymmetric Induction to the Hemisynthesis of Taxol and Analogues," Tetrahedron, vol. 45, No. 13, pp. 4177-4190 (1989).

Lin, T. et al., "Synthesis and Antiviral Activity of Various 3'-Azido,3'-Amino,2',3'-Unsaturated, and 2',3'-Dideoxy Analogues of Pyrimidine Deoxyribonucleosides against Retroviruses," J. Med. Chem., vol. 30, No. 2, pp. 440-444 (1987).

Murdock, K.C. et al., "Antitumor Agents. 1. 1,4-Bis[(aminoalkyl)amino]-9,10-anthracenediones," Journal of Medicinal Chemistry, vol. 22, No. 9, pp. 1024-1030 (1979).

McGuigan, C. et al., "Aryl Phosphoramidate Derivatives of d4T Have Improved Anti-HIV Efficacy in Tissue Culture and May Act by the Generation of a Novel Intracellular Metabolite," J. Med. Chem., vol. 39, No. 8, pp. 1748-1753 (1996).

Martin, J.C. et al., "9-[(1,3-Dihydroxy-2-propoxy)methyl]guanine: A New Potent and Selective Antiherpes Agent," J. Med. Chem., vol. 26, No. 5, pp. 759-761 (1983).

March, J., "Aliphatic Nucleophilic Substitution," Advanced Organic Chemistry, Chapter 10, pp. 348-357, 4th ed. John Wiley & Sons (1992).

Neuss, N. et al., "Vinca Alkaloids. XXI. The Structures of the Oncolytic Alkaloids Vinblastine (VLB) and Vincristine (VCR)," J. Am. Chem. Soc., vol. 86, pp. 1440-1442 (1964).

Noble, R.L. et al., "Role of Chance Observations in Chemotherapy: Vinca Rosea," Annals New York Academy of Sciences, vol. 76, pp. 882-894.

Nicolaou, K.C. et al., "Total synthesis of taxol," Nature, vol. 367, pp. 630-634 (1994).

Ogilvie, K.K. et al., "Biologically active acyclonucleoside analogues. II. The synthesis of 9-[[2-hydroxy-1-(hydroxymethypethoxy]methyl]guanine (BIOLF-62)," Can. J. Chem., vol. 60, pp. 3005-3010 (1982).

Oliveto, E.P. et al., "16-Alkylated Corticoids. III. 16B-Methyl-9a-Fluoroprednisolone 21-Acetate," J. Am. Chem. Soc., vol. 80, pp. 6687-6688 (1958).

Pandit, U.K. et al., "A New Class of Nucleoside Analogues. Synthesis of N1-Pyrimidynyl-and N9-Puriny1-4'-Hydroxy-3-(Hydroxymethyl) Butanes," Synthetic Communications, vol. 2, No. 6, pp. 345-351 (1972).

Penco, S., "Antitumour Anthracyclines: New Developments," Process Biochemistry, pp. 12-17 (1980).

Parkes, K.E.B., "Studies toward the Large-Scale Synthesis of the HIV Proteinase Inhibitor Ro 31-8959," J. Org. Chem., vol. 59, No. 13, pp. 3656-3664 (1994).

Rosenberg, I. et al., "Phosphonylmethoxyalkyl and Phosphonylalkyl Derivatives of Adenine," Collection Czechoslovak Chem. Commun., vol. 53, pp. 2753-2777 (1988).

Remiszewski, S.W. et al., "N-Hydroxy-3-phenyl-2-propenamides as Novel Inhibitors of Human Histone Deacetylase with in Vivo Antitumor Activity: Discovery of (2E)-N-Hydroxy-3-[4-[[(2-hydroxyethyl)[2-(1 H-indol-3-yl)ethyl]amino] methyl]-phenyl]-2-propenannide (NVP-LAQ824)," J. Med. Chem., vol. 46, No. 21, pp. 4609-4624 (2003).

Shannahoff, D.H. et al., "2,2'-Anhydropyrimidine Nucleosides. Novel Syntheses and Reactions," J. Org. Chem., vol. 38, No. 3, pp. 593-598 (1973).

Seeger, D.R. et al., "Analogs of Pteroylglutamic Acid. III. 4-Amino Derivatives," J. Am. Chem. Soc., vol. 71, pp. 1753-1758 (1949).

Schultze, L.M. et al., "Practical Synthesis of the anti-HIV Drug, PMPA," Tetrahedron Letters, vol. 39, pp. 1853-1856 (1998).

Sawada, S. et al., "Synthesis and Antitumor Activity of 20(S)-Camptothecin Derivatives: Carbamate-Linked, Water-Soluble Derivatives of 7-Ethyl-10-hydroxycamptothecin," Chem. Pharm. Bull., vol. 39, No. 6, pp. 1446-1454 (1991).

Smith, D.B. et al., "The Design, Synthesis, and Antiviral Activity of 4'-Azidocytidine Analogues against Hepatitis C Virus Replication: The Discovery of 4'-Azidoarabinocytidine," J. Med. Chem., vol. 52, No. 1, pp. 219-223 (2009).

Showalter, H.D.H. et al., "Adenosine Deaminase Inhibitors. Synthesis and Biological Evaluation of (±)-3,6,7,8Tetrahydro-3-[(92-hydroxyethoxy)methyl]imidazo[4,5-d][1,3]diazepin-8-ol and Some Selected C-5 Homologues of Pentostatin," J. Med. Chem., vol. 26, No. 10, pp. 1478-1482 (1983).

Smith, D.B. et al., "The Design, Synthesis, and Antiviral Activity of Monofluoro and Difluoro Analogues of 4'Azidocytidine Against Hepatitis C Virus Replication: the Discovery of 4'-Azido-2'-deoxy-2'-fluorocytidine and 4'- Azido-2'-dideoxy-2',2'-difluorocytidine," J. Med. Chem., vol. 52, No. 9, pp. 2971-2978 (2009).

Seeger, D.R. et al., "Antagonist for Pteroylglutamic Acid," J. Am. Chem. Soc., p. 2567 (1947).

Sawada, S. et al "Synthesis and Antitumor Activity of 20(S)-Camptothecin Derivatives: A-Ring Modifiied and 7,10-Disubstituted Camptothecins," Chem. Pharm. Bull., vol. 39, No. 12, pp. 3183-3188 (1991).

Smith, D.B. et al., "Design, synthesis, and antiviral properties of 4'-substituted ribonucleosides as inhibitors of hepatitis C virus replication: the discovery of R1479," Bioorganic & Medicinal Chemistry Letters, vol. 17, pp. 2570-2576 (2007).

Taub, D. et al., "16B-Methyl Cortical Steroids," J. Am. Chem. Soc., vol. 82, pp. 4012-4026 (1960).

Taub, D. et al., "16B-Methyl Cortical Steroids," J. Am. Chem. Soc., p. 4435 (1958).

Turner, S.R. et al., "Tipranavir (PNU-140690): a Potent, Orally Bioavailable Nonpeptidic HIV Protease Inhibitor of the 5,6-Dihydro-4-hydroxy-2-pyrone Sulfonamide Class," J. Med. Chem., vol. 41, No. 18, pp. 3467-3476 (1998).

Umezawa, H. et al., "Tetrahydropyranyl Derivatives of Daunomycin and Adriamycin," The Journal of Antibiotics, vol. XXXII, No. 10, pp. 1082-1084 (1979).

Valette, G. et al., "Decomposition Pathways and in Vitro HIV Inhibitory Effects of IsoddA Pronucleotides: Toward a Rational Approach for Intracellular Delivery of Nucleoside 5'-Monophosphates," J. Med. Chem., vol. 39, No. 10, pp. 1981-1990 (1996).

Venner, H., "Synthese der len natarlichen entsprechenden 2-Desoxy-Nucleoside des Adenins, Guanins and Hypoxanthins," Ber., pp. 140-149 (1960).

Walton, E. et al., "Branched-Chain Sugar Nucleosides. A New Type of Biologically Active Nucleoside," J. Am. Chem. Soc., vol. 88, No. 19, pp. 4524-4525 (1966).

Wani, M.G. et al., "Plant Antitumor Agents. 23. Synthesis and Antileukemic Activity of Camptothecin Analogues," J. Med. Chem., vol. 29, No. 11, pp. 2358-2363 (1986).

Wani, M.G. et al., "Plant Antitumor Agents. VI. The Isolation and Structure of Taxol, a Novel Antileukemic and Antitumor Agent from Taxus brevifolia," J. Am. Chem. Soc., vol. 93, No. 9, pp. 2325-2327 (1971).

Webb II, R.R. et al., "Synthesis of 2',3'-Dideoxyinosine," Nucleosides & Nucleotides, vol. 7, No. 2, pp. 147-153 (1988).

Woo, P.W.K. et al., "A Novel Adenosine and Ara-A Deaminase Inhibitor, (R)-3-(2-Deoxy-B-D-erythro-pentofuranosyl)-3,6,7,8-tetrahydroimidazo[4,5-d] [1,3] diazepin-8-ol," J. Heterocyclic Chem., vol. 11, pp. 641-643 (1974).

K. Wittine, et al., "The novel phosphoramidate derivatives of NSAID 3-hydroxypropylamides: Synthesis, cytostatic and antiviral activity evaluations", European J. Med. Chem. 44 (2009) 143-151.

T. Zhu, et al., "Design and synthesis of HCV agents with sequential triple inhibitory potentials", Bioorg. Med. Chem. Lett. 20 (2010) 5212-5216.

C. McGuigan, et al., "Design, synthesis and evaluation of a novel double pro-drug: INX-08189. A new clinical candidate for hepatitis C virus", Bioorg. Med. Chem. Lett. 20 (2010) 4850-4854.

Adelfinskaya, O., et al., "Polymerase-catalyzed synthesis of DNA from phosphoramidate conjugates of deoxynucleotides and amino acids," Nucleic Acids Research, vol. 35, No. 15, pp. 5060-5072 (2007).

* cited by examiner

NUCLEOSIDE ANALOGS

PRIORITY CLAIM

The present application claims priority to U.S. Provisional Patent Application No. 61/140,441, filed Dec. 23, 2008, the contents of which are incorporated by reference in its entirety.

FIELD OF THE INVENTION

The present invention pertains to nucleoside analogs and their use as agents for treating viral diseases. These compounds are inhibitors of RNA-dependent RNA viral replication and are useful as inhibitors of HCV NS5B polymerase, as inhibitors of HCV replication and for treatment of hepatitis C infection in mammals.

BACKGROUND

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 4.5 million infected people in the United States alone, according to the U.S. Center for Disease Control. According to the World Health Organization, there are more than 200 million infected individuals worldwide, with at least 3 to 4 million people being infected each year. Once infected, about 20% of people clear the virus, but the rest can harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their offspring. Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5B. The nonstructural (NS) proteins are believed to provide the catalytic machinery for viral replication. The NS3 protease releases NS5B, the RNA-dependent RNA polymerase from the polyprotein chain. HCV NS5B polymerase is required for the synthesis of a double-stranded RNA from a single-stranded viral RNA that serves as a template in the replication cycle of HCV. Therefore, NS5B polymerase is considered to be an essential component in the HCV replication complex (K. Ishi, et al, *Heptology*, 1999, 29: 1227-1235; V. Lohmann, et al., *Virology*, 1998, 249: 108-118). Inhibition of HCV NS5B polymerase prevents formation of the double-stranded HCV RNA and therefore constitutes an attractive approach to the development of HCV-specific antiviral therapies.

HCV belongs to a much larger family of viruses that share many common features.

Flaviviridae Viruses

The Flaviviridae family of viruses comprises at least three distinct genera: pestiviruses, which cause disease in cattle and pigs; flavivruses, which are the primary cause of diseases such as dengue fever and yellow fever; and hepaciviruses, whose sole member is HCV. The flavivirus genus includes more than 68 members separated into groups on the basis of serological relatedness (Calisher et al., *J. Gen. Virol*, 1993, 70, 37-43). Clinical symptoms vary and include fever, encephalitis and hemorrhagic fever (*Fields Virology*, Editors: Fields, B. N., Knipe, D. M., and Howley, P. M., Lippincott-Raven Publishers, Philadelphia, Pa., 1996, Chapter 31, 931-959). Flaviviruses of global concern that are associated with human disease include the Dengue Hemorrhagic Fever viruses (DHF), yellow fever virus, shock syndrome and Japanese encephalitis virus (Halstead, S. B., *Rev. Infect. Dis.*, 1984, 6, 251-264; Halstead, S. B., *Science*, 239:476-481, 1988; Monath, T. P., *New Eng. J. Med*, 1988, 319, 64 1-643).

The pestivirus genus includes bovine viral diarrhea virus (BVDV), classical swine fever virus (CSFV, also called hog cholera virus) and border disease virus (BDV) of sheep (Moennig, V. et al. *Adv. Vir. Res.* 1992, 41, 53-98). Pestivirus infections of domesticated livestock (cattle, pigs and sheep) cause significant economic losses worldwide. BVDV causes mucosal disease in cattle and is of significant economic importance to the livestock industry (Meyers, G. and Thiel, H. J., Advances in Virus Research, 1996, 47, 53-118; Moennig V., et al, Adv. Vir. Res. 1992, 41, 53-98). Human pestiviruses have not been as extensively characterized as the animal pestiviruses. However, serological surveys indicate considerable pestivirus exposure in humans.

Pestiviruses and hepaciviruses are closely related virus groups within the Flaviviridae family. Other closely related viruses in this family include the GB virus A, GB virus A-like agents, GB virus-B and GB virus-C (also called hepatitis G virus, HGV). The hepacivirus group (hepatitis C virus; HCV) consists of a number of closely related but genotypically distinguishable viruses that infect humans. There are at least 6 HCV genotypes and more than 50 subtypes. Due to the similarities between pestiviruses and hepaciviruses, combined with the poor ability of hepaciviruses to grow efficiently in cell culture, bovine viral diarrhea virus (BVDV) is often used as a surrogate to study the HCV virus.

The genetic organization of pestiviruses and hepaciviruses is very similar. These positive stranded RNA viruses possess a single large open reading frame (ORF) encoding all the viral proteins necessary for virus replication. These proteins are expressed as a polyprotein that is co- and post-translationally processed by both cellular and virus-encoded proteinases to yield the mature viral proteins. The viral proteins responsible for the replication of the viral genome RNA are located within approximately the carboxy-terminal. Two-thirds of the ORF are termed nonstructural (NS) proteins. The genetic organization and polyprotein processing of the nonstructural protein portion of the ORF for pestiviruses and hepaciviruses is very similar. For both the pestiviruses and hepaciviruses, the mature nonstructural (NS) proteins, in sequential order from the amino-terminus of the nonstructural protein coding region to the carboxy-terminus of the ORF, consist of p7, NS2, NS3, NS4A, NS4B, NS5A, and NS5B.

The NS proteins of pestiviruses and hepaciviruses share sequence domains that are characteristic of specific protein functions. For example, the NS3 proteins of viruses in both groups possess amino acid sequence motifs characteristic of serine proteinases and of helicases (Gorbalenya et al., *Nature*, 1988, 333, 22; Bazan and Fletterick *Virology*, 1989, 171, 637-639; Gorbalenya et al., *Nucleic Acid Res.*, 1989, 17, 3889-3897). Similarly, the NS5B proteins of pestiviruses and hepaciviruses have the motifs characteristic of RNA-directed RNA polymerases (Koonin, E. V. and Dolja, V. V., *Crir. Rev. Biochem. Molec. Biol.* 1993, 28, 375-430).

The actual roles and functions of the NS proteins of pestiviruses and hepaciviruses in the lifecycle of the viruses are directly analogous. In both cases, the NS3 serine proteinase is responsible for all proteolytic processing of polyprotein precursors downstream of its position in the ORF (Wiskerchen and Collett, *Virology*, 1991, 184, 341-350; Bartenschlager et al., *J. Virol.* 1993, 67, 3835-3844; Eckart et al. *Biochem. Biophys. Res. Comm.* 1993, 192, 399-406; Grakoui et al., *J. Virol.* 1993, 67, 2832-2843; Grakoui et al., *Proc. Natl. Acad. Sci. USA* 1993, 90, 10583-10587; Hijikata et al., *J. Virol.* 1993, 67, 4665-4675; Tome et al., *J. Virol.*, 1993, 67, 4017-4026). The NS4A protein, in both cases, acts as a cofactor with the NS3 serine protease (Bartenschlager et al., *J. Virol.* 1994, 68, 5045-5055; Fulla et al., *J. Virol.* 1994, 68, 3753-3760; Xu et al., *J. Virol.*, 1997, 71:53 12-5322). The NS3 protein of both viruses also functions as a helicase (Kim et al., *Biochem. Biophys. Res. Comm.*, 1995, 215, 160-166; Jin and Peterson, *Arch. Biochem. Biophys.*, 1995, 323, 47-53; Warrener and Collett, *J. Virol.* 1995, 69, 1720-1726). Finally, the NS5B proteins of pestiviruses and hepaciviruses have the predicted RNA-directed RNA polymerases activity (Behrens et al., EMBO, 1996, 15, 12-22; Lechmann et al., *J. Virol.*, 1997, 71, 8416-8428; Yuan et al., *Biochem. Biophys. Res. Comm.* 1997, 232, 231-235; Hagedorn, PCT WO 97/12033; Zhong et al, *J. Virol.*, 1998, 72, 9365-9369).

Currently, there are limited treatment options for individuals infected with hepatitis C virus. The current approved therapeutic option is the use of immunotherapy with recombinant interferon-α alone or in combination with the nucleoside analog ribavirin. This therapy is limited in its clinical effectiveness and only 50% of treated patients respond to therapy. Therefore, there is significant need for more effective and novel therapies to address the unmet medical need posed by HCV infection.

A number of potential molecular targets for drug development of direct acting antivirals as anti —HCV therapeutics have now been identified including, but not limited to, the NS2-NS3 autoprotease, the N3 protease, the N3 helicase and the NS5B polymerase. The RNA-dependent RNA polymerase is absolutely essential for replication of the single-stranded, positive sense, RNA genome and this enzyme has elicited significant interest among medicinal chemists.

Inhibitors of HCV NS5B as potential therapies for HCV infection have been reviewed: Tan, S.-L., et al., *Nature Rev. Drug Discov.*, 2002, 1, 867-881; Walker, M. P. et al., *Exp. Opin. Investigational Drugs*, 2003, 12, 1269-1280; Ni, Z-J., et al., *Current Opinion in Drug Discovery and Development*, 2004, 7, 446-459; Beaulieu, P. L., et al., *Current Opinion in Investigational Drugs*, 2004, 5, 838-850; Wu, J., et al., *Current Drug Targets-Infectious Disorders*, 2003, 3, 207-219; Griffith, R. C., et al, *Annual Reports in Medicinal Chemistry*, 2004, 39, 223-237; Carrol, S., et al., *Infectious Disorders-Drug Targets*, 2006, 6, 17-29. The potential for the emergence of resistant HCV strains and the need to identify agents with broad genotype coverage supports the need for continuing efforts to identify novel and more effective nucleosides as HCV NS5B inhibitors.

Nucleoside inhibitors of NS5B polymerase can act either as a non-natural substrate that results in chain termination or as a competitive inhibitor which competes with nucleotide binding to the polymerase. To function as a chain terminator the nucleoside analog must be taken up by the cell and converted in vivo to a triphosphate to compete for the polymerase nucleotide binding site. This conversion to the triphosphate is commonly mediated by cellular kinases which imparts additional structural requirements on a potential nucleoside polymerase inhibitor. Unfortunately, this limits the direct evaluation of nucleosides as inhibitors of HCV replication to cell-based assays capable of in situ phosphorylation.

In some cases, the biological activity of a nucleoside is hampered by its poor substrate characteristics for one or more of the kinases needed to convert it to the active triphosphate form. Formation of the monophosphate by a nucleoside kinase is generally viewed as the rate limiting step of the three phosphorylation events. To circumvent the need for the initial phosphorylation step in the metabolism of a nucleoside to the active triphosphate analog, the preparation of stable phosphate prodrugs has been reported. Nucleoside phosphoramidate prodrugs have been shown to be precursors of the active nucleoside triphosphate and to inhibit viral replication when administered to viral infected whole cells (McGuigan, C., et al., *J. Med. Chem.*, 1996, 39, 1748-1753; Valette, G., et al., *J. Med. Chem.*, 1996, 39, 1981-1990; Balzarini, J., et al., *Proc. National Acad Sci USA*, 1996, 93, 7295-7299; Siddiqui, A. Q., et al., *J. Med. Chem.*, 1999, 42, 4122-4128; Eisenberg, E. J., et al., *Nucleosides, Nucleotides and Nucleic Acids*, 2001, 20, 1091-1098; Lee, W. A., et al., *Antimicrobial Agents and Chemotherapy*, 2005, 49, 1898); US 2006/0241064; and WO 2007/095269.

Also limiting the utility of nucleosides as viable therapeutic agents is their sometimes poor physicochemical and pharmacokinetic properties. These poor properties can limit the intestinal absorption of an agent and limit uptake into the target tissue or cell. To improve on their properties, prodrugs of nucleosides have been employed. It has been demonstrated that preparation of nucleoside phosphoramidates improves the systemic absorption of a nucleoside and furthermore, the phosphoramidate moiety of these "pronucleotides" is masked with neutral lipophilic groups to obtain a suitable partition coefficient to optimize uptake and transport into the cell dramatically enhancing the intracellular concentration of the nucleoside monophosphate analog relative to administering the parent nucleoside alone. Enzyme-mediated hydrolysis of the phosphate ester moiety produces a nucleoside monophosphate wherein the rate limiting initial phosphorylation is unnecessary.

SUMMARY OF THE INVENTION

The present invention is directed to a purified compound represented by formula I or a purified compound represented by formula II:

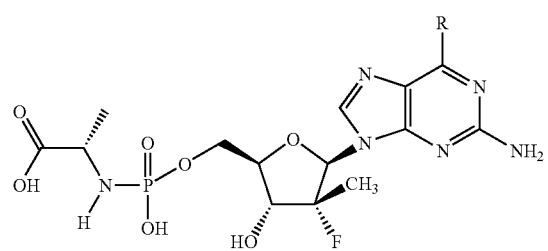

I

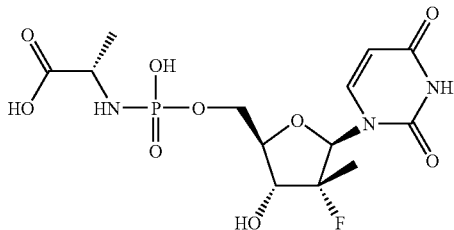

wherein R is OMe, OEt, —N(—CH₂CH₂CH₂—) (azetidin-1-yl), or OH;

or a salt, a pharmaceutically acceptable salt, a hydrate, a solvate, or a crystalline form thereof.

DEFINITIONS

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the first definition provided in the Summary of the Invention.

The term "purified," as described herein, refers to the purity of a given compound. For example, a compound is "purified" when the given compound is a major component of the composition, i.e., at least 50% w/w pure. Thus, "purified" embraces at least 50% w/w purity, at least 60% w/w purity, at least 70% purity, at least 80% purity, at least 85% purity, at least 90% purity, at least 92% purity, at least 94% purity, at least 96% purity, at least 97% purity, at least 98% purity, and at least 99% purity.

The term "metabolite," as described herein, refers to a compound produced in vivo after administration to a subject in need thereof.

The term "salt," as described herein, refers to a compound produced by the protonation of a proton-accepting moiety and/or deprotonation of a proton-donating moiety. It should be noted that protonation of the proton-accepting moiety results in the formation of a cationic species in which the charge is balanced by the presence of a physiological anion, whereas deprotonation of the proton-donating moiety results in the formation of an anionic species in which the charge is balanced by the presence of a physiological cation.

The term "P*" means that the phosphorous atom is chiral and that it has a corresponding Cahn-Ingold-Prelog designation of "R" or "S" which have their accepted plain meanings. It is contemplated that the phosphoramidate nucleoside represented by formula I and the cyclic phosphate nucleoside representend by formula II can exist as a mixture of diastereomers due to the chirality at phosphorous. Applicants contemplate use of the mixture of disastereomers and/or the resolved diastereomers. In some instances, an asterisk does not appear next to the phosphoroamidate or cyclic phosphate phosphorous atom. In these instances, it is understood that the phosphorous atom is chiral and that one of ordinary skill understands this to be so unless the substituents bound to the phosphorous exclude the possibility of chirality at phosphorous, such as in P(O)Cl₃.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use. The purified compounds of this invention can be administered alone but will generally be administered in admixture with one or more suitable pharmaceutical excipients, diluents or carriers selected with regard to the intended route of administration and standard pharmaceutical practice.

A "pharmaceutically acceptable salt" form of purified compound may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a purified compound as used herein means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as glycolic acid, pyruvic acid, lactic acid, malonic acid, malic acid, maleic acid, fumaric acid, tartaric acid, citric acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like or (2) basic addition salts formed with the conjugate bases of any of the inorganic acids listed above, wherein the conjugate bases comprise a cationic component selected from among $Na^+$, $K^+$, $Mg^{2+}$, $Ca^{2+}$, $NH_gR'''_{4-g}{}^+$, in which $R'''$ is a $C_{1-3}$ alkyl and g is a number selected from among 0, 1, 2, 3, or 4. It should be understood that all references to pharmaceutically acceptable salts include solvent addition forms (solvates) or crystal forms (polymorphs) as defined herein, of the same acid addition salt.

It is also contemplated that the compound represented by formula I or the compound represented by formula II embraces deuterated analogs. The term "deuterated analogs" means a compound described herein or its salts thereof, whereby a ¹H-isotope, i.e., hydrogen (H), is substituted by a ²H-isotope, i.e., deuterium (D). Deuterium substitution can be partial or complete. Partial deuterium substitution means that at least one hydrogen is substituted by at least one deuterium. For instance, for a compound represented by formula 14, one of ordinary skill can contemplate at least the following partial deuterated analogs (where "$d_n$" represents n-number of deuterium atoms, such as, for an isopropyl group n=1-7, while for a phenyl group, n=1-5). Although the methyl groups depicted below are shown as being completely deuterated, one will recognize that partial-deuterated variations are also possible, such as, —CDH₂ and —CD₂H.

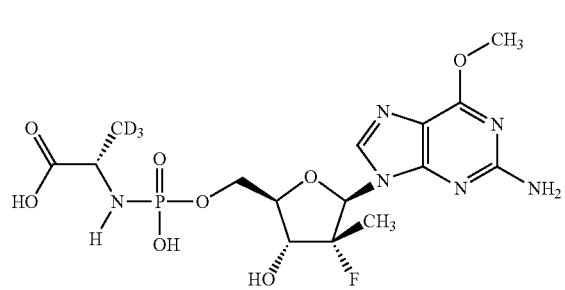

-continued

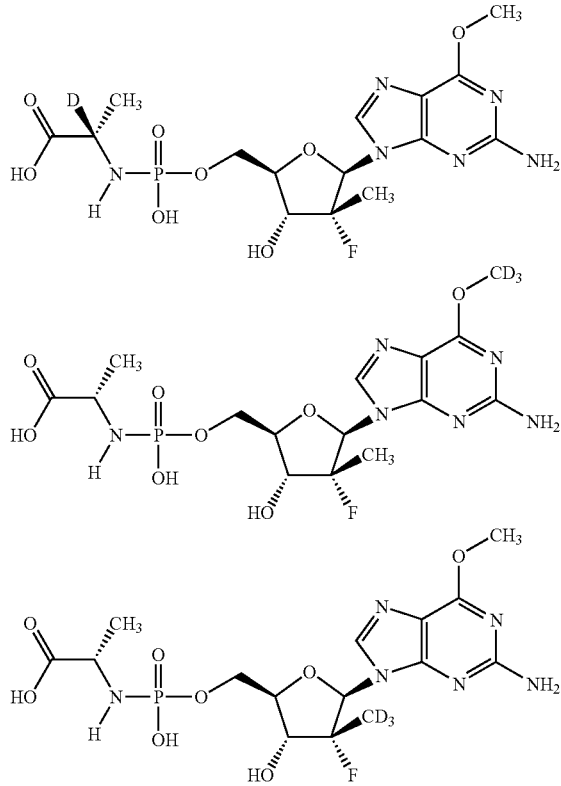

These are but a few deuterated analogs that are synthetically accessible by procedures and reagents that are known to one of ordinary skill.

DETAILED DESCRIPTION OF THE INVENTION

The present invention is directed to a purified compound represented by formula I or a purified compound represented by formula II:

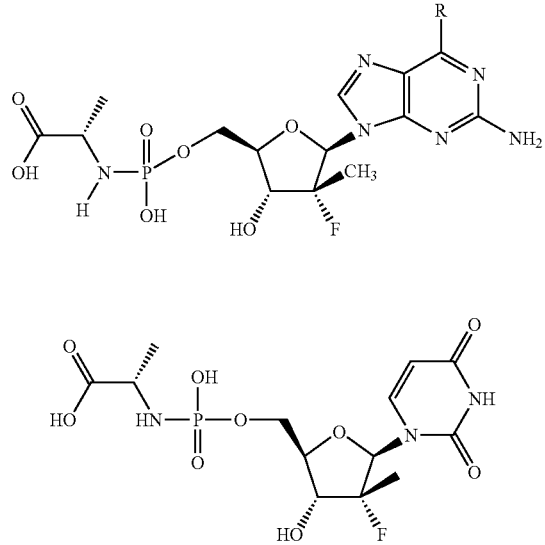

wherein R is OMe, OEt, —N(—CH$_2$CH$_2$CH$_2$—) (azetidin-1-yl), or OH;

or a salt, a pharmaceutically acceptable salt, a hydrate, a solvate, or a crystalline form thereof.

A first embodiment of the present invention is directed to a purified compound represented by formula I

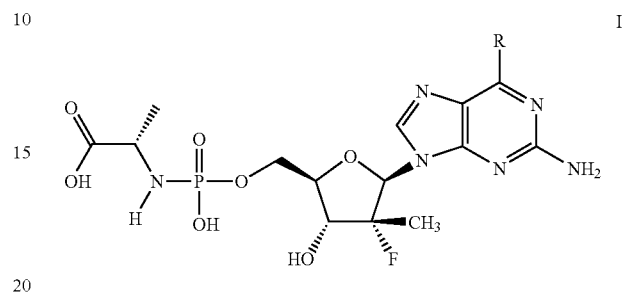

wherein R is OMe;

or a salt, a pharmaceutically acceptable salt, a hydrate, a solvate, or a crystalline form thereof.

A first embodiment of the present invention is directed to a purified compound represented by formula I

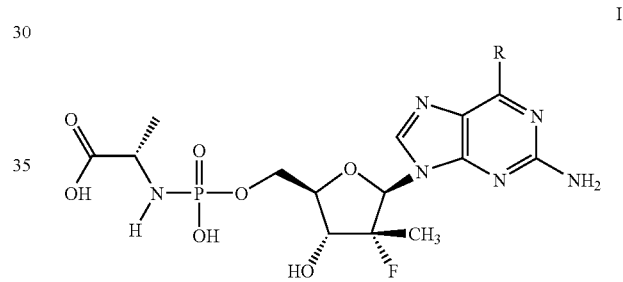

wherein R is OEt;

or a salt, a pharmaceutically acceptable salt, a hydrate, a solvate, or a crystalline form thereof A third embodiment of the present invention is directed to a purified compound represented by formula I

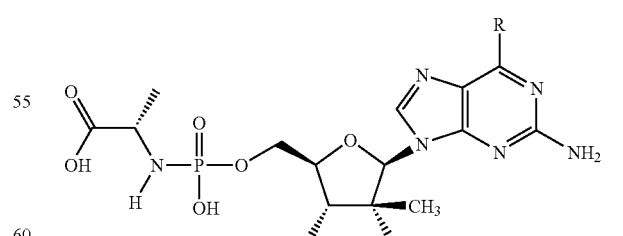

wherein R is OH;

or a salt, a pharmaceutically acceptable salt, a hydrate, a solvate, or a crystalline form thereof.

A fourth embodiment of the present invention is directed to a purified compound represented by formula I

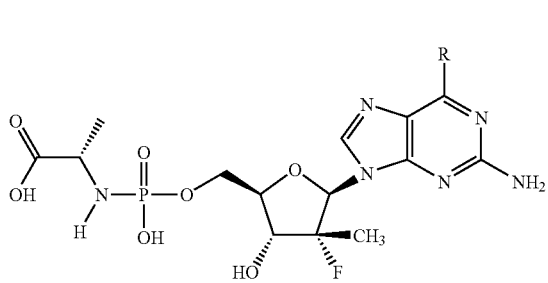

wherein R is —N(—CH$_2$CH$_2$CH$_2$—) (azetidin-1-yl);
or a salt, a pharmaceutically acceptable salt, a hydrate, a solvate, or a crystalline form thereof.

A fifth embodiment of the present invention is directed to a purified compound represented by formula II

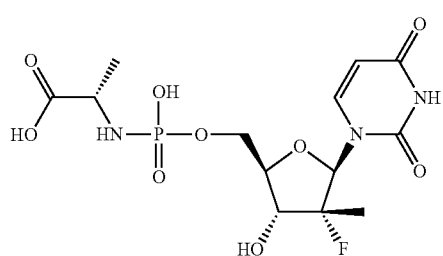

or a salt, a pharmaceutically acceptable salt, a hydrate, a solvate, or a crystalline form thereof.

Dosage, Administration, and Use

A sixth embodiment of the present invention is directed to a composition for the treatment of any of the viral agents disclosed herein said composition comprising a pharmaceutically acceptable medium selected from among an excipient, carrier, diluent, or equivalent medium and a purified compound represented by formula I or a purified compound represented by formula II, or a salt, a pharmaceutically acceptable salt, a hydrate, a solvate, or a crystalline form thereof.

It is contemplated that the formulation of the sixth embodiment can contain any of the purified compounds contemplated in the present invention either alone or in combination with another purified compound of the present invention.

The purified compounds of the present invention may be formulated in a wide variety of oral administration dosage forms and carriers. Oral administration can be in the form of tablets, coated tablets, hard and soft gelatin capsules, solutions, emulsions, syrups, or suspensions. Compounds of the present invention are efficacious when administered by suppository administration, among other routes of administration. The most convenient manner of administration is generally oral using a convenient daily dosing regimen which can be adjusted according to the severity of the disease and the patient's response to the antiviral medication.

A purified compound or purified compounds of the present invention, as well as their pharmaceutically acceptable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as suspensions, emulsions, or filled capsules for oral use; or in the form of suppositories for rectal or vaginal administration. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the desired dose and pharmacokinetic parameters.

Solid form preparations include, for example, powders, tablets, pills, capsules, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like. Examples of solid formulations are exemplified in EP 0524579; U.S. Pat. No. 6,635,278; US 2007/0099902; U.S. Pat. No. 7,060,294; US 2006/0188570; US 2007/0077295; US 2004/0224917; U.S. Pat. No. 7,462,608; US 2006/0057196; U.S. Pat. Nos. 6,267,985; 6,294,192; 6,569,463; 6,923,988; US 2006/0034937; U.S. Pat. Nos. 6,383,471; 6,395,300; 6,645,528; 6,932,983; US 2002/0142050; US 2005/0048116; US 2005/0058710; US 2007/0026073; US 2007/0059360; and US 2008/0014228, each of which is incorporated by reference.

Liquid formulations also are suitable for oral administration include liquid formulation including emulsions, syrups, elixirs and aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous suspensions can be prepared by dispersing the finely divided active component in water with viscous material, such as natural or synthetic gums, resins, methylcellulose, sodium carboxymethylcellulose, and other well known suspending agents.

The purified compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The purified compounds of the present invention may be formulated for vaginal administration. Pessaries, tampons, creams, gels, pastes, foams or sprays containing in addition to the active ingredient such carriers as are known in the art to be appropriate.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa., which is hereby incorporated by reference. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (e.g., salt formulation), which are well within the ordinary skill in the art. It is also well within the ordinary skill of the art to modify the route of administration and dosage regimen of a particular compound in order to manage the pharmacokinetics of the present purified compounds for maximum beneficial effect in patients.

Additionally, the purified compounds of the present invention may be formulated in conjunction with liposomes or micelles. As to liposomes, it is contemplated that the purified compounds can be formulated in a manner as disclosed in U.S. Pat. Nos. 5,013,556; 5,213,804; 5,225,212; 5,891,468; 6,224,903; 6,180,134; 5,192,549; 5,316,771; 4,797,285; 5,376,380; 6,060,080; 6,132,763; 6,653,455; 6,680,068; 7,060,689; 7,070,801; 5,077,057; 5,277,914; 5,549,910; 5,567,434; 5,077,056; 5,154,930; 5,736,155; 5,827,533; 5,882,679; 6,143,321; 6,200,598; 6,296,870; 6,726,925; and 6,214,375, each of which is incorporated by reference. As to micelles, it is contemplated that the purified compounds can be formulated in a manner as disclosed in U.S. Pat. Nos. 5,145,684 and 5,091,188, both of which are incorporated by reference.

A seventh embodiment of the present invention is directed to a use of a purified compound represented by formula I or a purified compound represented by formula II, or a salt, a pharmaceutically acceptable salt, a hydrate, a solvate, or a crystalline form thereof, in the manufacture of a medicament for the treatment of any condition the result of an infection by any one of the following viral agents: hepatitis C virus, West Nile virus, yellow fever virus, degue virus, rhinovirus, polio virus, hepatitis A virus, bovine viral diarrhea virus and Japanese encephalitis virus.

The term "medicament" means a substance used in a method of treatment and/or prophylaxis of a subject in need thereof, wherein the substance includes, but is not limited to, a composition, a formulation, a dosage form, and the like, comprising the compound of formula I. It is contemplated that the use of the compound represented by formula I in the manufacture of a medicament, for the treatment of any of the antiviral conditions disclosed herein, either alone or in combination with another compound of the present invention. A medicament includes, but is not limited to, any one of the compositions contemplated by the seventh embodiment of the present invention.

An eighth embodiment of the present invention is directed to a method of treatment and/or prophylaxis in a subject in need thereof said method comprises administering a therapeutically effective amount of a purified compound represented by formula I or a purified compound represented by formula II, or a salt, a pharmaceutically acceptable salt, a hydrate, a solvate, or a crystalline form thereof to the subject.

A first aspect of the eighth embodiment is directed to a method of treatment and/or prophylaxis in a subject in need thereof said method comprises administering a therapeutically effective amount of at least two compounds falling within the scope of a purified compound represented by formula I or a purified compound represented by formula II, or a salt, a pharmaceutically acceptable salt, a hydrate, a solvate, or a crystalline form thereof to the subject.

A second aspect of the eighth embodiment is directed to a method of treatment and/or prophylaxis in a subject in need thereof said method comprises alternatively or concurrently administering a therapeutically effective amount of at least two compounds falling within the scope of a purified compound represented by formula I or a purified compound represented by formula II, or a salt, a pharmaceutically acceptable salt, a hydrate, a solvate, or a crystalline form thereof to the subject.

It is intended that a subject in need thereof is one that has any condition the result of an infection by any of the viral agents disclosed herein, which includes, but is not limited to, hepatitis C virus, West Nile virus, yellow fever virus, degue virus, rhinovirus, polio virus, hepatitis A virus, bovine viral diarrhea virus or Japanese encephalitis virus, flaviviridae viruses or pestiviruses or hepaciviruses or a viral agent causing symptoms equivalent or comparable to any of the above-listed viruses.

The term "subject" means a mammal, which includes, but is not limited to, cattle, pigs, sheep, chicken, turkey, buffalo, llama, ostrich, dogs, cats, and humans, preferably the subject is a human. It is contemplated that in the method of treating a subject thereof of the ninth embodiment can be any of the compounds contemplated herein, either alone or in combination with another compound of the present invention.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.001 and about 10 g, including all values in between, such as 0.001, 0.0025, 0.005, 0.0075, 0.01, 0.025, 0.050, 0.075, 0.1, 0.125, 0.150, 0.175, 0.2, 0.25, 0.5, 0.75, 1, 1.5, 2, 2.5, 3, 3.5, 4, 4.5, 5, 5.5, 6, 6.5, 7, 7.5, 8, 8.5, 9, and 9.5, per day should be appropriate in monotherapy and/or in combination therapy. A particular daily dosage is between about 0.01 and about 1 g per day, including all incremental values of 0.01 g (i.e., 10 mg) in between, a preferred daily dosage about 0.01 and about 0.8 g per day, more preferably about 0.01 and about 0.6 g per day, and most preferably about 0.01 and about 0.25 g per day, each of which including all incremental values of 0.01 g in between. Generally, treatment is initiated with a large initial "loading dose" to rapidly reduce or eliminate the virus following by a decreasing the dose to a level sufficient to prevent resurgence of the infection. One of ordinary skill in treating diseases described herein will be able, without undue experimentation and in reliance on personal knowledge, experience and the disclosures of this application, to ascertain a therapeutically effective amount of the compounds of the present invention for a given disease and patient.

Therapeutic efficacy can be ascertained from tests of liver function including, but not limited to protein levels such as serum proteins (e.g., albumin, clotting factors, alkaline phosphatase, aminotransferases (e.g., alanine transaminase, aspartate transaminase), 5'-nucleosidase, γ-glutaminyl-transpeptidase, etc.), synthesis of bilirubin, synthesis of cholesterol, and synthesis of bile acids; a liver metabolic function, including, but not limited to, carbohydrate metabolism, amino acid and ammonia metabolism. Alternatively the therapeutic effectiveness may be monitored by measuring HCV-RNA. The results of these tests will allow the dose to be optimized.

A third aspect of the eighth embodiment, is directed to a method of treatment and/or prophylaxis in a subject in need thereof said method comprises administering to the subject a therapeutically effective amount of a purified compound represented by formula I or a purified compound represented by formula II, or a salt, a pharmaceutically acceptable salt, a hydrate, a solvate, or a crystalline form thereof and a therapeutically effective amount of another antiviral agent; wherein the administration is concurrent or alternative. It is understood that the time between alternative administration can range between 1-24 hours, which includes any sub-range in between including, 2, 3, 4, 5, 6, 7, 8, 9, 10, 11, 12, 13, 14, 15, 16, 17, 18, 19, 20, 21, 22, and 23 hours. Examples of "another antiviral agent" include, but are not limited to: HCV NS3 protease inhibitors (see WO 2008010921, WO 2008010921, EP 1881001, WO 2007015824, WO 2007014925, WO 2007014926, WO 2007014921, WO 2007014920, WO 2007014922, US 2005267018, WO 2005095403, WO 2005037214, WO 2004094452, US 2003187018, WO 200364456, WO 2005028502, and WO 2003006490); HCV NS5B Inhibitors (see US 2007275947, US20072759300, WO2007095269, WO 2007092000, WO 2007076034, WO 200702602, US 2005-98125, WO 2006093801, US 2006166964, WO 2006065590, WO 2006065335, US 2006040927, US 2006040890, WO 2006020082, WO 2006012078, WO 2005123087, US 2005154056, US 2004229840, WO 2004065367, WO 2004003138, WO 2004002977, WO 2004002944, WO 2004002940, WO 2004000858, WO 2003105770, WO 2003010141, WO 2002057425, WO 2002057287, WO 2005021568, WO 2004041201, US 20060293306, US 20060194749, US 20060241064, U.S. Pat. No. 6,784,166, WO 2007088148, WO 2007039142, WO 2005103045, WO 2007039145, WO 2004096210, and WO 2003037895); HCV NS4 Inhibitors (see WO 2007070556 and WO 2005067900); HCV NS5a Inhibitors (see US 2006276511, WO 2006120252, WO 2006120251, WO 2006100310, WO 2006035061); Toll-like receptor agonists (see WO 2007093901); and other inhibitors (see WO 2004035571, WO 2004014852, WO 2004014313, WO 2004009020, WO 2003101993, WO 2000006529); and compounds disclosed in U.S. patent application Ser. No. 12/053,015, filed Mar. 21, 2008 (the contents of which are incorporated by reference).

A fourth aspect of the eighth embodiment, is directed to a method of treatment and/or prophylaxis in a subject in need thereof said method comprises alternatively or concurrently administering a therapeutically effective amount of a purified compound represented by formula I or a purified compound represented by formula II, or a salt, a pharmaceutically acceptable salt, a hydrate, a solvate, or a crystalline form thereof to the subject. It is understood that the time between alternative administration can range between 1-24 hours, which includes any sub-range in between including, 2, 3, 4, 5, 6, 7, 8, 9, 10, 11, 12, 13, 14, 15, 16, 17, 18, 19, 20, 21, 22, and 23 hours.

It is contemplated that the another antiviral agent such as interferon-α, interferon-β, pegylated interferon-α, ribavirin, levovirin, viramidine, another nucleoside HCV polymerase inhibitor, a HCV non-nucleoside polymerase inhibitor, a HCV protease inhibitor, a HCV helicase inhibitor or a HCV fusion inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It should be noted that for the purified compounds disclosed herein may form metabolites upon administration to a subject in need thereof. For instance, the phosphoramidate moiety may undergo hydrolysis to form a monophosphate derivative, which may then undergo phosphorylation to provide the diphosphate and the triphosphate derivative, which under physiological conditions would be present in the form of physiological salts. As metabolites or metabolite salts are contemplated herein, it is also contemplated as an alternative embodiment a method of treatment in a patient in need thereof contacting at least one metabolite obtained from the purified compound represented by formula I or at least one metabolite obtained from the purified compound represented by formula II with at least one hepatitis C virus infected cell.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

EXAMPLES

A further understanding of the disclosed embodiments will be appreciated by consideration of the following examples, which are only meant to be illustrative, and not limit the disclosed invention.

Disclosed $^1$H-NMR values were recorded on a Varian AS-400 instrument. Mass spectral data were obtained using either a Micromass-Quattromicro API or a Waters Acquity.

UPLC analysis: Acquity HPLC BEH C18 1.7 μm 2.1×50 mm column; 0 to 2 min, 5 to 95% (0.1% formic acid in acetonitrile) in 0.1% formic acid in water; 2 to 2.4 min, 95 to 5% (0.1% formic acid in acetonitrile) in 0.1% formic acid in water; 2.4 to 3 min, 5% (0.1% formic acid in acetonitrile) in 0.1% formic acid in water.

The following scheme is intended to serve as a visual aid for the following discussion and is not intended to limit the scope of the appended claims. A general procedure for preparing phosphoramidate nucleosides is disclosed in U.S. patent application Ser. No. 12/053,015, filed Mar. 21, 2008, now U.S. Pat. No. 7,964,580 at pages 651-655, the contents of which are herin incorporated by reference.

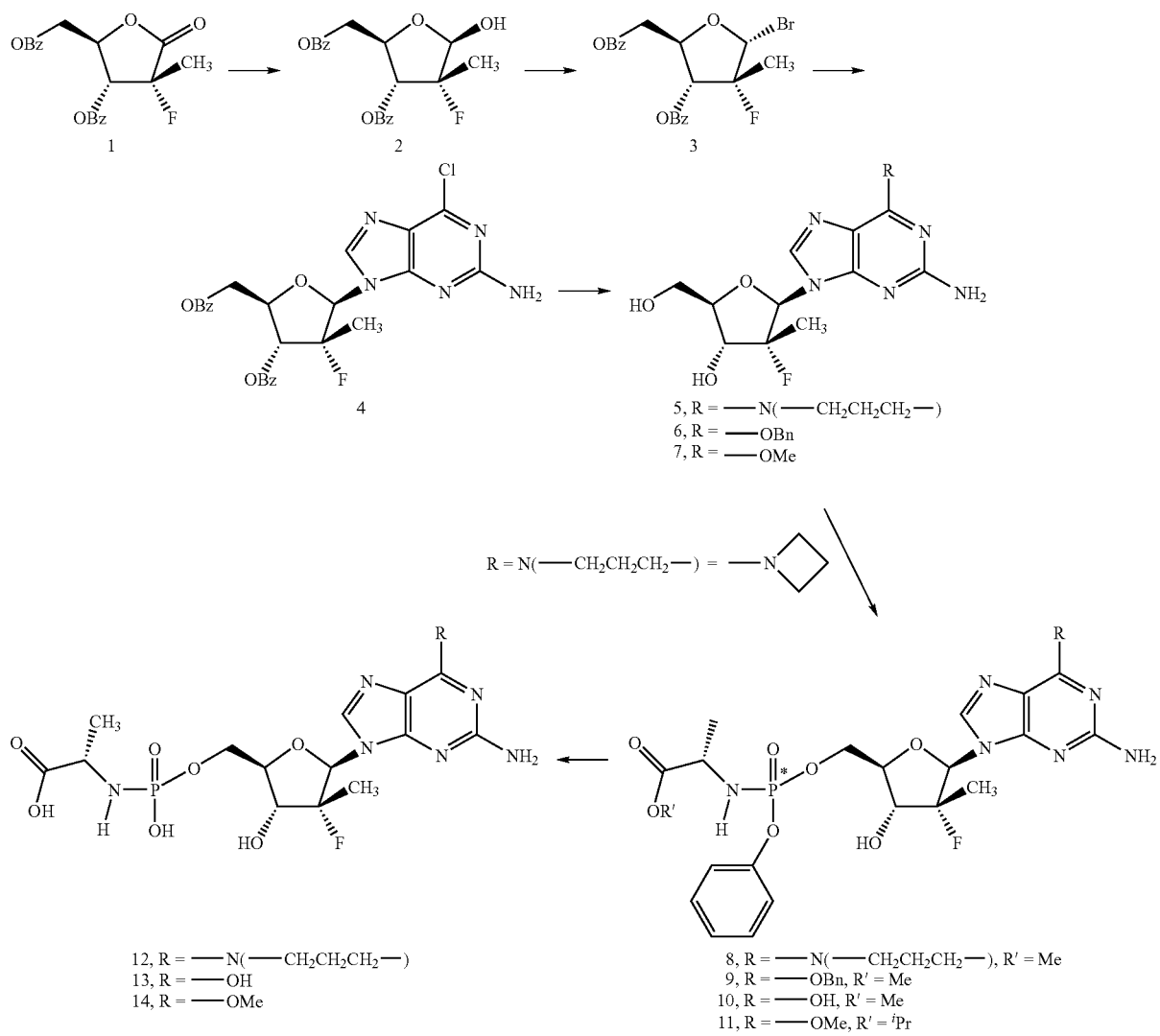

Compound (1) can be obtained by a process disclosed at page 5 in U.S. Published Application No. 2008/0139802 (which corresponds to WO 2008/045419), at pages 11-13 in WO 2006/012440, and at pages 20-22 and 30-31 in WO 2006/031725, each of which is hereby incorporated by reference.

Synthesis of ((2R,3R,4R,5R)-3-(benzoyloxy)-4-fluoro-5-hydroxy-4-methyltetrahydrofuran-2-yl)methyl benzoate (2)

To a 5 L of dry three-neck round-bottomed flask fit with a mechanical stirrer, addition funnel and thermometer was charged the lactone ((2R,3R,4R)-3-(benzoyloxy)-4-fluoro-4-methyl-5-oxotetrahydrofuran-2-yl)methyl benzoate) (1, 379 g, 1.018 mol). The solid was dissolved in anhydrous THF (1.75 L) and cooled to −30° C. under a nitrogen atmosphere. A solution of lithium tri-tert-butoxyaluminohydride (1.0 M in THF, 1.527 L) was added to the lactone solution while stirring over 1 h and maintaining the −30° C. temperature. After finishing the addition, the temperature was slowly increased and the reaction was followed by TLC (lactol $R_f$ 0.4, 30% EtOAc in hexanes). The reaction was complete after 1 h 15 min (temperature reached −10° C.). The reaction was quenched by addition of Ethyl acetate (900 mL) via addition funnel. Sat. NH$_4$Cl (40 mL) was added at 0° C. The cloudy mixture was decanted into a 10 L round-bottomed flask. The solid residue left behind was filtered and washed with ethyl acetate (2×200 mL). The filtrate was combined with the decanted solution and the combined solution was concentrated under reduced pressure. The oily residue was dissolved in ethyl acetate (2 L) and washed with 3 N HCl (600 mL). The aqueous layer was back-extracted with ethyl acetate (3×400 mL). The combined organic layer was washed with water (3×800 mL), sat. NaHCO$_3$ (400 mL) and brine (400 mL). The organic solution was dried over MgSO$_4$, filtered and concentrated under reduced pressure to afford a light brown oily residue. The residue was purified by plug column (2.2 kg of 40-63 micron silica gel, packed in a 6 L sintered glass funnel, 22 cm length of silica gel, diameter 15 cm) using suction and a step-gradient of 5%, 10%, 20%, and 30% ethyl acetate in hexanes-ca 5 L of each). The product containing fractions were combined and concentrated under reduced pressure to a colorless, very thick liquid (310.4 g).

The liquid slowly solidified after adding crystalline beta product as seeds (ca 100 mg spread out) under vacuum (0.2 mmHg) at 50° C. The process of solidification was complete in 20 hours at 50° C. with or without vacuum. The white solid thus collected (293.8 g, 77%) has a mp of 79-80° C. and ratio of β/α is 20:1 based on NMR.

$^1$H-NMR (DMSO-d$_6$) β-isomer, δ=5.20 (dd, 1 H, OH); α-isomer, δ=5.40 (dd, 1 H, OH). (β-lactol). (DMSO-d$_6$): δ 7.99 (m, 2 H, arom.), 7.93 (m, 2 H, arom.), 7.70 (m, 1 H, arom.), 7.61 (m, 1 H, arom.), 7.55 (m, 2 H, arom.), 7.42 (m, 2 H, arom.), 7.32 (dd, 1 H, C1-H), 5.54 (dd, 1 H, C3-H), 5.20 (dd, 1 H, OH), 4.55-4.50 (m, 1 H, C5-Ha), 4.46-4.40 (m, 2 H, C5-Hb and C4-H), 1.42 (d, 3 H, CH$_3$).

Synthesis of ((2R,3R,4R,5R)-3-(benzoyloxy)-5-bromo-4-fluoro-4-methyltetrahydrofuran-2-yl)methyl benzoate (3)

Anhydrous dichloromethane (5.6 L) was charged into a reactor and cooled to −22° C. or below. Triphenylphosphine (205.4 g, 0.783 mol) was added to the cold solvent and the suspension was stirred to form a solution. The lactol (2, 209.4 g, 0.559 mol) in solid form was added to the cold solution and stirred for 15 mins. Carbon tetrabromide (278.2 g, 0.839 mol) was added portion-wise while maintaining the temperature of the solution between −22° C. to −20° C. under a flow of nitrogen gas (approx. 30 min). After finishing the addition of CBr$_4$, the temperature was slowly raised to −17° C. over 20 mins. The reaction was judged to be >95% complete by TLC (R$_f$s 0.61 (α), 0.72 (β), 0.36 lactol; 20% EtOAc in hexanes). The reaction solution was immediately transferred to a vessel containing 230 g of flash chromatography grade silica gel (40-63 microns). The stirred mixture was immediately passed through a pad of silica gel (680 g) in a 2.5 L sintered glass Buchner funnel. The filtrate was concentrated under reduced pressure to about 800 mL and the ratio of α/β isomers of the crude product was 10:1 as determined by $^1$H-NMR. (CDCl$_3$) δ=6.35, (s, α C1-H), 6.43, (d, β C1-H). The residue was purified by plug column chromatography using 2.1 kg of silica gel in a 6 L sintered glass Buchner funnel and eluted (via suction) with a stepwise gradient elution of 1%, 5%, 8% 12% EtOAc in hexane (ca 4 L each) to remove non-polar impurities followed by 12%, 25% EtOAc in hexane (6 L total) to elute the product. The product containing fractions were combined into two fractions, concentrated under reduced pressure, dried under vacuum (0.1 mmHg, ambient temp., 20 h) to colorless oils. Main fraction (197 g, 89% α/β=20:1). The alpha isomer crystallized from a small portion of the oil upon standing at 0° C. for several weeks to give large, thin plates, mp 59-61° C. The pure beta isomer crystallized from a mixture of alpha and beta product oil from an earlier less selective run to give needles, mp 77-79° C.

$^1$H-NMR (β-bromide) (CDCl$_3$): δ=8.08 (m, 2 H, arom.), 8.04 (m, 2 H, arom.), 7.62 (m, 1H, arom.), 7.54-7.45 (m, 3 H, arom.), 7.35 (m, 2 H, arom.), 6.43 (d, 1 H, C1-H), 6.04 (dd, 1 H, C3-H), 4.78-4.73 (m, 2 H, C4-H and C5-Ha), 4.63-4.58 (m, 1 H, C5-Hb), 1.76 (d, 3 H, CH$_3$). α-bromide, α/β=20:1) (CDCl$_3$): δ 8.13 (m, 2 H, arom.), 8.02 (m, 2 H, arom.), 7.63-7.56 (m, 2 H, arom.), 7.50-7.42 (m, 4 H, arom.), 6.34 (s, 1 H, C1-H), 5.29 (dd, 1 H, C3-H), 4.88 (m, 1 H, C4-H), 4.78 (dd, 1 H, C5-Ha), 4.63 (dd, 1 H, C5-Hb), 1.72 (d, 3 H, CH$_3$).

Synthesis of (2R,3R,4R,5R)-5-(2-amino-6-chloro-9H-purin-9-yl)-2-(benzoyloxymethyl)-4-fluoro-4-methyltetrahydrofuran-3-yl benzoate (4)

To a 12 L of three-neck round-bottomed flask was charged 6-chloro-2-aminopurine (225.4 g, 1.329 mol). Anhydrous tert-BuOH (4.5 L) was added and the solution was stirred with a mechanical stirrer at ambient temperature. Potassium tert-butoxide (solid, 151.6 g, 1.35 mol) was added portion-wise under a flow of nitrogen gas while stirring. The mixture was stirred at RT for an additional 30 min. To a 5 L round-bottomed flask was loaded the α-bromide (3, 197 g, 0.451 mol) and 3 L of anhydrous acetonitrile at ambient temperature. The bromide solution was added to the purine base suspension over 1 min at ambient temperature. The 5 L flask was rinsed with acetonitrile (2×μL) to transfer bromide completely to the reaction mixture. The mixture was heated gradually to 50° C. over 2 h with a heating mantle and controller, and stirred for 20 h. The reaction was almost complete as shown by TLC beta (R$_f$ 0.28, 30% EtOAc in hexanes). The reaction was quenched by the addition of sat. NH$_4$Cl (200 mL) to form a suspension. The suspended solid[1] was removed by filtration through a 3 cm pad of Celite in a 2.5 L porcelain Buchner funnel. The solid was washed with toluene (3×100 mL). The combined filtrate was neutralized by adding 6 N HCl solution until pH 7 (approx 220 mL). The mixture was concentrated under reduced pressure. When the volume of mixture was reduced to about one-third volume, additional precipitated solid was removed by filtration in a similar manner. The filtrate was further concentrated to a volume of about 800 mL. The residue was loaded onto a plug column (1.6 kg flash grade silica gel in a 6 L sintered glass Buchner funnel) and eluted (via suction) with a gradient of 10% ethyl acetate in hexanes (6 L) to remove non-polar impurities, 30% ethyl acetate in hexanes to afford a small amount of lactol (6 L), and then 40%~45% ethyl acetate in hexanes (4 L) to elute the main amount of product. The product containing fractions were combined, concentrated under reduced pressure and dried under vacuum (0.2 mmHg, 24 h, ambient temp.) to a white foam solid (150.7 g, β/α=14:1 by NMR.

$^1$H-NMR. (CDCl$_3$) beta: δ=1.33 (d, 22.4 Hz, 2'-C—CH$_3$), alpha: 1.55 (d, 22 Hz, 2'-C—CH$_3$).

The product mixture foam was dissolved in methanol (700 mL) at ambient temperature. Upon standing, a solid slowly formed over 2 h. The suspension was cooled in a freezer to −5° C. for 17 h. The resulting white solid was collected by filtration and washed with cold MeOH (−5° C., 3×60 mL) and ethyl ether (3×100 mL). The solid was dried under vacuum (0.2 mmHg, 24 h, ambient temp.) to afford 110.5 g of β-product with excellent de (β/α 99.8:1 by HPLC). The filtrate was partially concentrated (ca. 400 mL) and then diluted with more MeOH (400 mL) while heating to 60° C. The solution was cooled down to ambient temperature, seeded and the cooled to −5° C. The second crop was collected, washed and dried in a similar manner to give more product as a white solid (12.26 g) with similar diastereomeric purity. The mother liquor was concentrated to dryness under reduced pressure (ca. 25 g). The residue was a mixture of β and α-isomers. It was subjected to automated silica gel column chromatography (Analogix, 240 g cartridge, 40% to 50% ethyl acetate in hexanes) to afford 14.52 g of product foam which was recrystallized from MeOH, washed and dried in a similar manner to afford an additional 8.46 g of product in high purity.

The three solids were judged to be of similar purity and they were combined to give 131.2 g of white crystalline product 4, (55% from bromosugar, 49% from lactol). Mp 160.5-162.0° C. HPLC purity 99.5% including 0.20% alpha.

$^1$H-NMR (pure β-anomer, CDCl$_3$): δ=8.03 (m, 2 H, arom.), 7.93 (m, 2 H, arom.), 7.88 (s, 1 H, C8-H), 7.60 (m, 1 H, arom.), 7.50 (m, 1 H, arom.), 7.44 (m, 2 H, arom.), 7.33 (m, 2 H, arom.), 6.44 (dd, 1 H, C1'-H), 6.12 (d, 1 H, C3'-H), 5.35 (s, 2 H, NH$_2$), 5.00 (dd, 1 H, C5'-Ha), 4.76 (m, 1 H, C4'-H), 4.59 (dd, 1 H, C5'-Hb), 1.33 (d, 3 H, CH$_3$).

¹H-NMR (α-isomer, CDCl₃): δ=8.11-8.09 (m, 3 H, arom. and C8-H), 8.01 (m, 2 H, arom.), 7.63 (m, 1 H, arom.), 7.55 (m, 1 H, arom.), 7.48 (m, 2 H, arom.), 7.39 (m, 2 H, arom.), 6.35 (d, 1 H, C1'-H), 5.76 (dd, 1 H, C3'-H), 5.18 (s, 2 H, NH₂), 4.93-4.89 (m, 1 H, C4'-H), 4.75-4.71 (m, 1 H, C5'-Ha), 4.58-4.54 (m, 1 H, C5'-Hb), 1.55 (d, 3 H, CH₃).

Synthesis of (2R,3R,4R,5R)-5-(2-amino-6-(azetidin-1-yl)-9H-purin-9-yl)-4-fluoro-2-(hydroxymethyl)-4-methyltetrahydrofuran-3-ol (5)

To a 350 mL of dry seal pressure flask (Chemglass) were added (2R,3R,4R,5R)-5-(2-amino-6-chloro-9H-purin-9-yl)-2-(benzoyloxymethyl)-4-fluoro-4-methyltetrahydrofuran-3-yl benzoate (4, 3.6 g, 6.85 mmol) and 150 mL of absolute ethanol. Azetidine hydrochloride (2.56 g, 27.4 mmol) was added and then followed by triethylamine (4.16 g, 41.1 mmol). The supension was stirred and heated to 70° C. while sealed for 5 hours. All the starting material was consumed but the benzoyl groups remained as shown by TLC. Sodium methoxide (7.8 mL, 34.3 mmol, 25% solution in methanol) was added to the mixture and heated at 50° C. The reaction was complete after 3.5 h. The reaction mixture was allowed to cool to room temperature and neutralized by addition of glacial acetic acid (0.41 g, 6.85 mmol). The mixture was concentrated under reduced pressure and then the residue was triturated with ethyl acetate. The resulting solid was removed by filtration and the solid was washed with EtOAc (2×15 mL). The filtrate was concentrated under reduced pressure and the residue was purified via column chromatography (Analogix, 120 g cartridge, gradient of 0 to 15% MeOH in DCM). The pure product containing fractions were combined, concentrated under reduced pressure and dried (50° C., 0.2 mmHg, 17 h) to a light pink colored foam solid (2.15 g, 6.35 mmol, 93%).

¹H-NMR (DMSO-d₆) δ=8.00 (s, 1 H, C8-H), 6.03 (s, 2 H, NH₂), 6.00 (d, 1 H, C1'-H), 5.64 (d, 1 H, 3'-OH), 5.24 (t, 1 H, 5'-OH), 4.24-4.10 (m, 5 H, N—CH₂ of azetidine, C3'-H), 3.90-3.81 (m, 2 H, C4'-H and C5'-H$_a$), 3.69-3.64 (m, 1 H, C5'-H$_b$), 2.37 (penta, 2 H, center CH₂ of azetidine), 1.05 (d, 3 H, C2'-CH₃).

Synthesis of (2R,3R,4R,5R)-5-(2-amino-6-(benzyloxy)-9H-purin-9-yl)-4-fluoro-2-(hydroxymethyl)-4-methyltetrahydrofuran-3-ol (6)

To a 500 mL of dry round-bottomed flask were added (2R,3R,4R,5R)-5-(2-amino-6-chloro-9H-purin-9-yl)-2-(benzoyloxymethyl)-4-fluoro-4-methyltetrahydrofuran-3-yl benzoate (4, 8.0 g, 15.2 mmol) and anhydrous benzyl alcohol (128 mL). To another 250 mL of dry round-bottomed flask were charged NaH (60% in mineral oil, 2.44 g, 60.8 mmol) and anhydrous DMF (40 mL). The suspension was stirred at 0° C. in an ice-water bath. Benzyl alcohol (27 mL) was added drop-wise via a syringe. A solution was slowly formed and it was transferred to the nucleoside suspension quickly under a nitrogen atmosphere at room temperature. The mixture was heated to 50° C. and stirred. The reaction was complete after 3 h and cooled to ambient temperature. It was neutralized by the addition of 4 NHCl to ca. pH=7 (12 mL). The solution was concentrated under reduced pressure (4 mbar, 90° C. bath). The cloudy residue was diluted with dichloromethane (100 mL) and washed with water (3×30 mL), brine (30 mL) and dried over Na₂SO₄. The suspension was filtered and the filtrate was concentrated under reduced pressure to an oily residue. This was purified by column chromatography (Analogix, 0 to 8% gradient of MeOH in DCM). The product eluted at 4% MeOH in DCM. The product containing fractions were combined, concentrated under reduced pressure and dried (50° C., 0.2 mmHg, 17 h) to a white foam solid (4.57 g, 11.7 mmol, 77.2%).

¹H-NMR (DMSO-d₆) δ=8.18 (s, 1 H, 8-H), 7.53-7.51 (m, 2 H, arom-H), 7.43-7.34 (m, 3 H, arom-H), 6.66 (s, 2 H, NH₂), 6.05 (d, 1 H, C1'-H), 5.67 (d, 1 H, 3'-OH), 5.48 (dd, 2 H, CH₂ of Benzyl), 5.25 (t, 1 H, 5'-OH), 4.18 (dt, 1 H, C3'-H), 3.92-3.82 (m, 2 H, C4'-H and C5'-H$_a$), 3.71-3.66 (m, 1 H, C5'-H$_b$), 1.07 (d, 3 H, C2'-CH₃).

Synthesis of (2R,3R,4R,5R)-5-(2-amino-6-methoxy-9H-purin-9-yl)-4-fluoro-2-(hydroxymethyl)-4-methyltetrahydrofuran-3-ol (7)

To a suspension of 4 (500 mg, 0.951 mmol) in MeOH (10 ml) was added NaOMe in MeOH (25%, 0.90 ml). The mixture was heated to 50° C. for 3 h. Then, it was neutralized with AcOH. It was concentrated and EtOAC (30 ml) was added. The insoluble solid was filtered off The filtrate was concentrated and purified by flash column chromatography on silica gel using 0 to 15% MeOH in CH₂Cl₂ as eluents. Compound 7 (203 mg, 68.3%) was obtained as a white solid: ¹H NMR (400 MHz, DMSO-d₆) δ 8.17 (s, 1H), 6.61 (s, 2H), 6.05 (d, J=17.6 Hz, 1H), 5.67 (d, J=7.2 Hz, 1H), 5.25 (t, J=4.8 Hz, 1H), 4.18 (dt, J=25.6, 8.0 Hz, 1H), 3.96 (s, 3H), 3.91 (dm, J=9.2 Hz, 1H), 3.85 (ddd, J=2.0, 5.2, 12.8 Hz, 1H), 3.69 (ddd, J=2.8, 3.2, 12.0 Hz, 1H), 1.06 (d, J=22.8 Hz, 3H); tR=0.52 (99.1%); LRMS (ESI) [M+H]⁺ calculated for C₁₂H₁₇FN₅O₄ 314.3, found 314.2.

Synthesis of (2S)-methyl 2-((((2R,3R,4R,5R)-5-(2-amino-6-(azetidin-1-yl)-9H-purin-9-yl)-4-fluoro-3-hydroxy-4-methyltetrahydrofuran-2-yl)methoxy)(phenoxy)phosphorylamino)-propanoate (8)

To a 100 mL dry round-bottomed flask were added phenyl dichlorophosphate (1.72 g, 8.15 mmol) and anhydrous dichloromethane (17 mL). The amino ester (1.42 g, 10.2 mmol) was added and the suspension was cooled to −5° C. N-Methylimidazole (3.34 g, 40.7 mmol) was added via a syringe in one portion and the solution was stirred at −5° C. for 1 h under a nitrogen atmosphere. The nucleoside (5, 1.38 g, 4.07 mmol) (foam solid) was then added in one portion and the solution was allowed to warm up over 1 h to ambient temperature. After 4 h at ambient temperature, TLC (5% MeOH in DCM) indicated an incomplete reaction (about 30% SM remained) but also a growing less polar impurity. The reaction was quenched by the addition of sat NH₄Cl (20 mL) and diluted with dichloromethane (20 mL). The organic layer was separated and washed with water (5×30 mL), brine (20 mL) and dried over Na₂SO₄. The product containing solution was filtered and concentrated under reduced pressure to a crude oily residue, 3.26 g. This was purified by column chromatography (Analogix, 40 g cartridge, gradient of MeOH in DCM from 0% to 10%). The product eluted at 4% MeOH in DCM. The pure product containing fractions were combined, concentrated under reduced pressure and dried (50° C., 0.2 mmHg, 17 h) to a white foam solid (1.322 g, 2.28 mmol, 56%). HPLC purity 99.25%. NMR spectra of product showed it is a mixture of two diastereoisomers with a ratio of 55:45.

¹H-NMR (DMSO-d₆) δ=7.80 (s, 1 H, 8-H of one isomer), 7.80 (s, 1 H, 8-H of another isomer), 7.38-7.33 (m, 2 H, arom-H), 7.22-7.14 (m, 3 H, arom-H), 6.09 (s, 2 H, NH₂), 6.12-6.02 (m, 2 H, C1'-H and NH), 5.83 (d, 1 H, 3'-OH of one isomer), 5.77 (d, 1 H, 3'-OH of another isomer), 4.46-4.05 (m, 8 H, NCH$_2$ of azetidine, α-H of aminoester, C3'-H, C4'-H, C5'-H$_a$), 3.89-3.79 (m, 1 H, C5'-H$_b$), 3.56 (s, 3 H, OCH$_3$ of aminoester in one isomer), 3.54 (s, 3 H, OCH$_3$ of aminoester in another isomer), 2.37 (penta, 2 H, center CH$_2$ of azetidine), 1.21 (d, 3 H, α-CH$_3$ of aminoester in one isomer), 1.19 (d, 3 H, α-CH$_3$ of aminoester in another isomer), 1.08 (d, 3 H, C2'-CH$_3$).

$^{31}$P NMR (DMSO-d$_6$): δ 4.85 (one isomer), 4.77 (other isomer).

Synthesis of (2S)-methyl 2-(((((2R,3R,4R,5R)-5-(2-amino-6-(benzyloxy)-9H-purin-9-yl)-4-fluoro-3-hydroxy-4-methyltetrahydrofuran-2-yl)methoxy)(phenoxy)phosphorylamino)-propanoate (9)

To a 100 mL of dry round-bottomed flask are charged phenyl dichlorophosphate (3.29 g, 15.58 mmol) and anhydrous dichloromethane (24 mL). The aminoester tosylate (white powder) is added and the solution was cooled to −5° C. under nitrogen. N-Methylimidazole (4.92 g, 59.94 mmol) is added via a dry syringe in one portion and the resulted colorless clear solution is stirred at −5° C. for one hour. Then the nucleoside (6) solid is added (2.334 g, 5.99 mmol) to the solution under nitrogen in one portion and the mixture is allowed to warm to ambient temperature to give a colorless solution. Reaction progress is monitored by TLC (5% methanol in dichloromethane). The reaction is still quenched by the addition of dichloromethane (30 mL) and 1 N HCl (60 mL). The organic layer is separated and the aqueous layer is extracted with dichloromethane (2×20 mL). The combined organic layer is washed with water (2×40 mL), sat NaHCO$_3$ (30 mL), water, and brine. The organic layer is dried over Na$_2$SO$_4$. After removal of solid by filtration, the filtrate is concentrated under reduced pressure to a gummy residue (7.28 g). The residue is purified via column chromatography (Analogix, 80 g cartridge, gradient of 0 to 10% MeOH in DCM). The product is eluted at 2% MeOH in DCM. The product containing fractions are combined and are concentrated under reduced pressure and are dried (50° C., 0.2 mmHg, 17 h) to a white foam solid. A portion of the starting nucleoside (0.257 g) is also recovered. Yield is based on consumed starting material.

Synthesis of (2S)-methyl 2-(((((2R,3R,4R,5R)-5-(2-amino-6-hydroxy-9H-purin-9-yl)-4-fluoro-3-hydroxy-4-methyltetrahydrofuran-2-yl)methoxy)(phenoxy)phosphorylamino)-propanoate (10)

To a 250 mL of dry round-bottomed flask with starting material (9, 1.92 g, 2.8 mmol) is added anhydrous absolute ethanol (50 mL). Palladium on charcoal (10%, 120 mg) is added. The atmosphere in the flask is exchanged with hydrogen and the mixture is stirred under 1 atm of hydrogen gas for 3.5 h at room temperature. The reaction is judged complete by TLC and the Pd on charcoal is removed by filtration and is washed with ethanol (2×10 mL). The filtrate is concentrated under reduced pressure to a solid residue. The solid is mixed with silica gel (10 g) and is purified by column chromatography (Analogix, 40 g cartridge, gradient of 1% to 16% MeOH in DCM). The product containing fractions are combined, concentrated under reduced pressure and are dried (50° C., 0.2 mmHg, 17 h) to a white powder (1.43 g, 86%). HPLC purity 99.55%.

Synthesis of (2S)-isopropyl 2-(((((2R,3R,4R,5R)-5-(2-amino-6-methoxy-9H-purin-9-yl)-4-fluoro-3-hydroxy-4-methyltetrahydrofuran-2-yl)methoxy)(phenoxy)phosphorylamino)-propanoate (11)

To a solution of the 7 (50 mg, 0.16 mmol) and N-methylimidazole (0.10 ml, 1.3 mmol) in THF (1.5 ml) was added the phosphorochloridate in THF (1.0 M, 0.48 ml) at 0° C. dropwise. The reaction was slowly warmed to room temperature and stirred for 1 h. Then water (0.1 ml) and EtOAc (5 ml) was added. The organic solution was washed with sat. aq. sodium citrate mono basic (2 ml×2), sat. aq. NaHCO$_3$ (2 mL×1), dried (MgSO$_4$) and concentrated. The crude oil was purified by flash column chromatography on silica gel using 0 to 8% iPrOH in CH$_2$Cl$_2$ as eluents to give the phosphoramidate (36 mg, 39%, 2:1 mixture of diastereomers) as a white solid: $^1$H NMR (400 MHz, DMSO-d$_6$) δ 7.97 (s, 0.66H), 7.95 (s, 0.34H), 7.39-7.30 (m, 2H), 7.25-7.13 (m, 3H), 6.63 (bs, 2H), 6.11 (d, J=18.8 Hz, 0.34H), 6.09 (d, J=19.2 Hz, 0.66H), 6.06-5.88 (m, 1H), 5.90-5.78 (m, 1H), 4.80 (septet, J=6.8 Hz, 1H), 4.45-4.24 (m, 3H), 4.16-4.05 (m, 1H), 3.96 (s, 3H), 3.84-3.70 (m, 1H), 1.28-1.03 (m including d at 1.20 with J=7.2 Hz, 12H); $^{31}$P NMR (162 MHz, DMSO-d$_6$) δ 4.91, 4.72; tR=1.16 (33.1%), 1.18 (63.9%); LRMS (ESI) [M+H]$^+$ calculated for C$_{24}$H$_{33}$FN$_6$O$_8$P 583.5, found 583.4.

Synthesis of (2S)-2-(((((2R,3R,4R,5R)-5-(2-amino-6-(azetidin-1-yl)-9H-purin-9-yl)-4-fluoro-3-hydroxy-4-methyltetrahydrofuran-2-yl)methoxy)(hydroxy)phosphorylamino)propanoic acid (12)

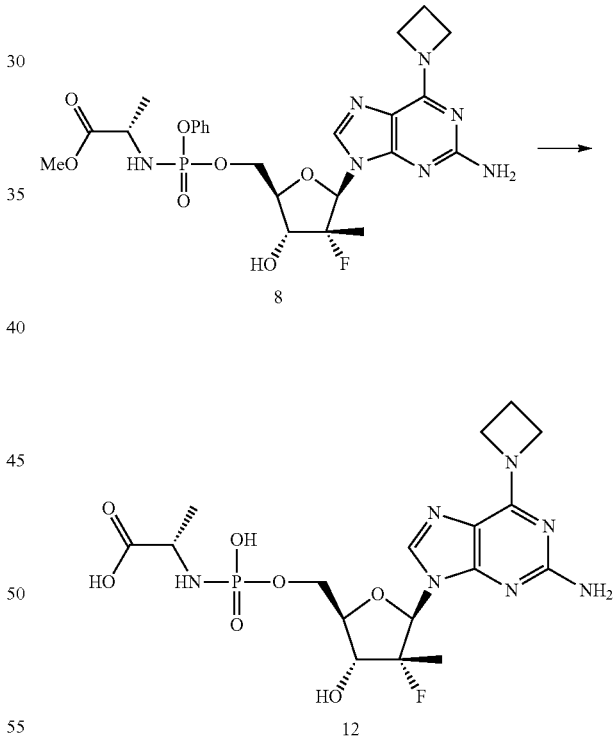

Compound 8 (150 mg, 0.269 mmol) was suspended in triethylamine (2 mL) and water (0.5 mL), and heated at 60° C. for 20 h. Volatile components were then evaporated under reduced pressure. The crude product was purified by flash column chromatography on silica gel using 0 to 15% NH$_4$OH in iPrOH as eluents. The product was obtained as a white solid (101 mg, 80%): $^1$H NMR (400 MHz, DMSO-d$_6$) δ 7.93 (s, 1H), 6.10 (bs, 2H), 5.97 (d, J=17.2 Hz, 1H), 4.44-3.86 (m, 10H), 2.37 (quintet, J=7.6 Hz, 2H), 1.10 (d, J=6.8 Hz, 3H), 1.05 (d, J=22.4 Hz, 3H); $^{31}$P NMR (162 MHz, DMSO-d$_6$) δ

8.72; tR=0.55 (97.4%); LRMS (ESI) [M+H]+ calculated for C17H26FN7O7P 490.4, found 490.4.

Synthesis of (2S)-2-((((2R,3R,4R,5R)-5-(2-amino-6-hydroxy-9H-purin-9-yl)-4-fluoro-3-hydroxy-4-methyltetrahydrofuran-2-yl)methoxy)(hydroxy)phosphorylamino)propanoic acid (13)

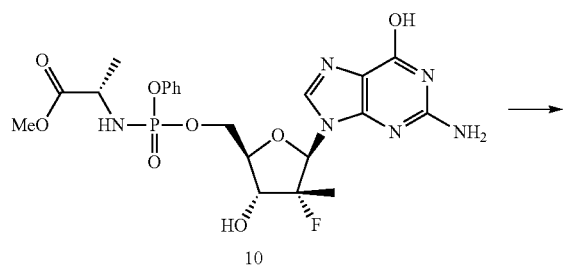

10

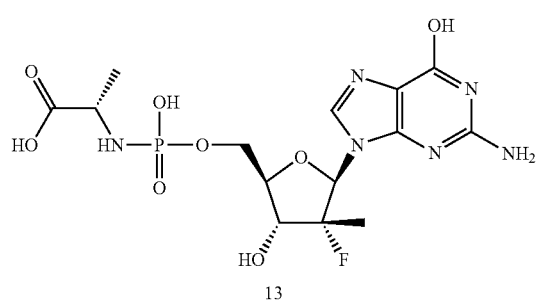

13

Compound 10 (110 mg, 0.204 mmol) was suspended in triethylamine (2 mL) and water (0.5 mL), and heated at 60° C. for 20 h. The volatile components were then evaporated under reduced pressure. The crude product was purified by flash column chromatography on silica gel using 0 to 20% NH4OH in iPrOH as eluents. The product was obtained as a white solid (74 mg, 81%): $^1$H NMR (400 MHz, DMSO-$d_6$) δ 7.88 (s, 1H), 6.68 (bs, 2H), 5.93 (d, J=18.0 Hz, 1H), 4.42-3.83 (m, 6H), 1.11 (d, J=7.2 Hz, 3H), 1.07 (d, J=22.4 Hz, 3H); $^{31}$P NMR (162 MHz, DMSO-$d_6$) δ 8.90; tR=0.50 (98.7%); LRMS (ESI) [M+H]+ calculated for C14H21FN6O8P 451.3, found 451.3.

Synthesis of (2S)-2-((((2R,3R,4R,5R)-5-(2-amino-6-methoxy-9H-purin-9-yl)-4-fluoro-3-hydroxy-4-methyltetrahydrofuran-2-yl)methoxy)(hydroxy)phosphorylamino)propanoic acid (14)

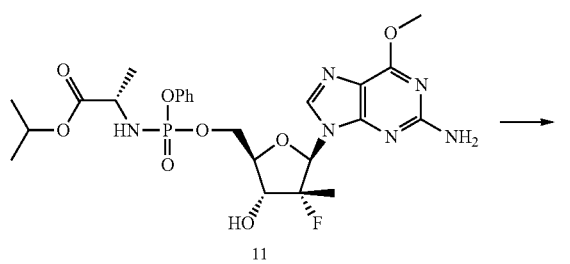

11

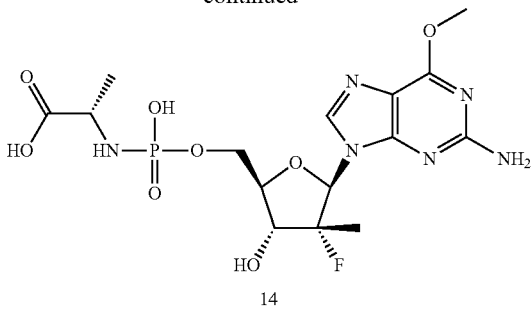

14

Compound 11 (110 mg, 0.189 mmol) was suspended in triethylamine (2 mL) and water (0.5 mL), and heated at 60° C. for 48 h. The volatile components were then evaporated under reduced pressure. The crude product was purified by flash column chromatography on silica gel using 0 to 20% NH4OH in iPrOH as eluents. The product was obtained as a white solid (88 mg, 97%): $^1$H NMR (400 MHz, DMSO-$d_6$) δ 8.08 (s, 1H), 6.67 (bs, 2H), 6.03 (d, J=18.0 Hz, 1H), 4.44-3.70 (m including s at 3.96, 8H), 3.39 (m, 1H), 1.10 (d, J=7.2 Hz, 3H), 1.05 (d, J=22.8 Hz, 3H); $^{31}$P NMR (162 MHz, DMSO-$d_6$) δ 8.52; tR=0.61 (96.3%); LRMS (ESI) [M+H]+ calculated for C15H23FN6O8P 465.3, found 465.3.

Synthesis of (2S)-2-((((2R,3R,4R,5R)-5-(2-amino-6-ethoxy-9H-purin-9-yl)-4-fluoro-3-hydroxy-4-methyltetrahydrofuran-2-yl)methoxy)(hydroxy)phosphorylamino)propanoic acid (15)

It is contemplated that compound 15 is prepared in a manner analogous to compound 14.

Synthesis of (2S)-2-((((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(hydroxy)phosphorylamino)propanoic acid (17)

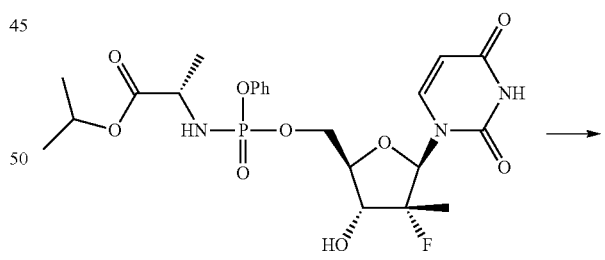

16

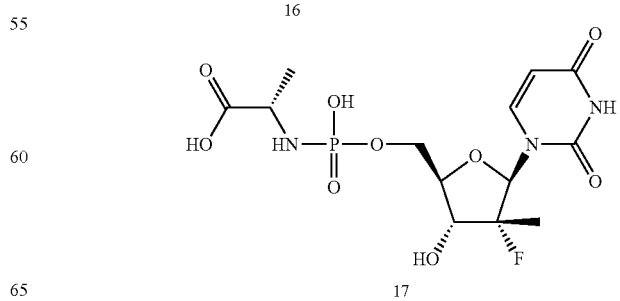

17

Compound 16 ((2S)-isopropyl 2-(4(2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy)phosphoryl-amino)propanoate) was prepared according to the procedures disclosed at pages 652-669 of U.S. patent application Ser. No. 12/053,015 filed Mar. 21, 2008 the identified subject matter of which is incorporated by reference in its entirety. (Compound 16 is Identified as Compound 25 at Page 674 of 12/053,015.)

Compound 17 was synthesis from compound 15 by the following procedure. Compound 16 (300 mg, 0.57 mmol) was suspended in triethylamine (6 mL) and water (1.5 mL), and heated at 60° C. for 30 h. The volatile components were then evaporated under reduced pressure. The crude product was purified by flash column chromatography on silica gel using 50-70% isopropyl alcohol in dichloromethane followed by 0-20% ammonium hydroxide in isopropyl alcohol as eluents. The product (2) was obtained as a white solid (210 mg, 92% yield): $^1$H NMR (400 MHz, DMSO-$d_6$) δ 8.01 (d, J=8.0 Hz, 1H), 5.97 (d, J=18.8 Hz, 1H), 5.55 (d, J=8.0 Hz, 1H), 4.02-3.80 (m, 4H), 3.34 (dq, J=7.2, 10.4 Hz, 1H), 1.25 (d, J=22.4 Hz, 3H), 1.10 (d, J=6.8 Hz, 3H); $^{31}$P NMR (162 MHz, DMSO-$d_6$) δ 7.91; MS (ESI) (M+H)$^+$ 412.3.

It is contemplated that the purified compounds disclosed herein are active against hepatitis C virus.

The contents of U.S. patent application Ser. No. 12/053,015, filed Mar. 21, 2008 now U.S. Pat. No. 7,964,580(see also WO 2008/121634), U.S. patent application Ser. No. 12/479,075, filed Jun. 5, 2009, now U.S. Pat. No. 8,173,621, and U.S. Provisional Patent Application Nos. 61/060,683, filed Jun. 11, 2008, 61/140,423 and 61/140,317, each of which being filed Dec. 23, 2008 are hereby incorporated by reference in their entirety. Moreover, the patent and non-patent references disclosed herein are incorporated by reference. In the event that the incorporated subject matter contains a term that conflicts with a term disclosed in the present application text, the meaning of the term contained in the present application controls provided that the overall meaning of the incorporated subject matter is not lost.

The invention claimed is:

1. A purified compound represented by formula I or a purified compound represented by formula II, or a salt or pharmaceutically acceptable salt thereof:

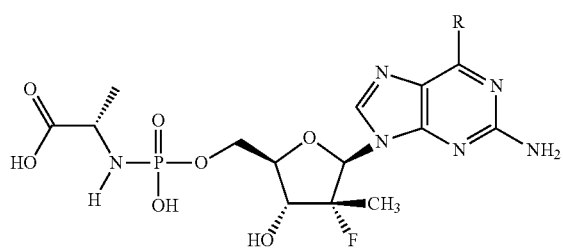

I

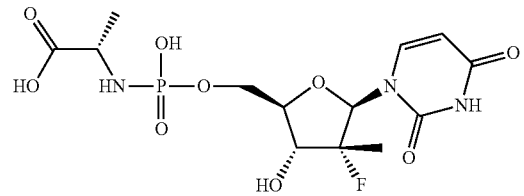

II wherein R is OMe, OEt, —N(—CH$_2$CH$_2$CH$_2$—), or OH.

2. The purified compound of claim 1 represented by formula I

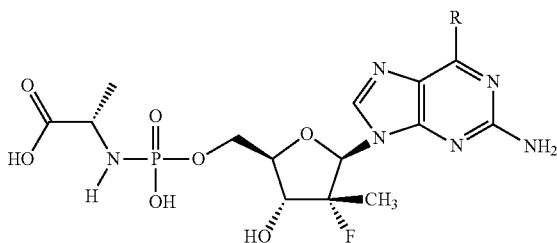

I wherein R is OMe.

3. The purified compound of claim 1 represented by formula I

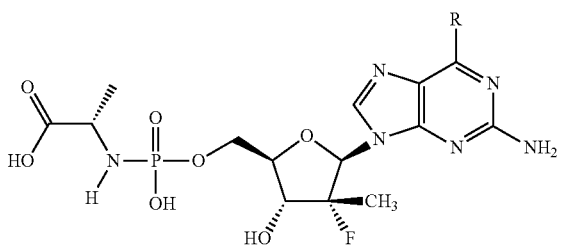

I wherein R is OEt.

4. The purified compound of claim 1 represented by formula I

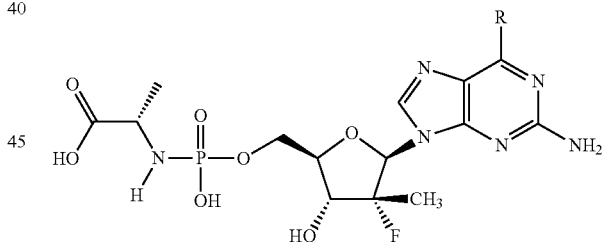

I wherein R is OH.

5. The purified compound of claim 1 represented by formula I

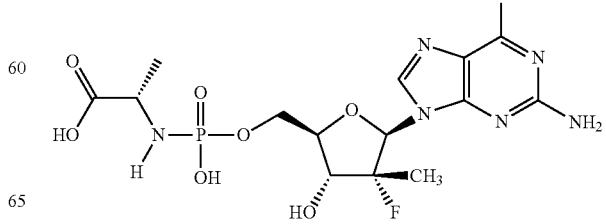

I wherein R is —N(—CH$_2$CH$_2$CH$_2$—).

6. The purified compound of claim 1 represented by formula II

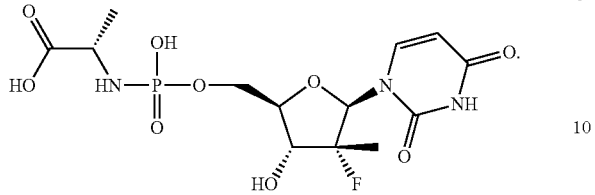

7. A pharmaceutical composition comprising the compound according to claim 1.

8. A method of treatment of a subject infected with a virus selected from the group consisting of hepatitis C virus, West Nile virus, yellow fever virus, dengue virus, rhinovirus, polio virus, hepatitis A virus, bovine viral diarrhea virus or Japanese encephalitis virus which comprises administering to the subject a therapeutically effective amount of the compound according to claim 1.

9. The method of treatment according to claim 8 wherein the virus is hepatitis C virus.

10. A method of treatment in a subject in need thereof, which comprises contacting at least one hepatitis C virus infected cell with at least one compound according to claim 1.

* * * * *